(12) United States Patent
Steinkogler et al.

(10) Patent No.: US 8,146,149 B2
(45) Date of Patent: Mar. 27, 2012

(54) APPARATUS AND METHOD FOR PROTECTING A MEDICAL DEVICE AND A PATIENT TREATED WITH THIS DEVICE AGAINST HARMFUL INFLUENCES FROM A COMMUNICATION NETWORK

(75) Inventors: Alexander Steinkogler, Munich (DE); Hans Martin Lauer, Munich (DE); Niko Preus, Himmelkron (DE)

(73) Assignee: B. Braun Medizinelectronik GmbH & Co. KG, Puchheim (DE)

( * ) Notice: Subject to any disclaimer, the term of this patent is extended or adjusted under 35 U.S.C. 154(b) by 0 days.

(21) Appl. No.: 11/757,188

(22) Filed: Jun. 1, 2007

(65) Prior Publication Data

US 2008/0040788 A1 Feb. 14, 2008

(30) Foreign Application Priority Data

Jun. 3, 2006 (DE) .......................... 10 2006 026 088
May 25, 2007 (DE) .......................... 10 2007 024 720

(51) Int. Cl.
*G06F 21/00* (2006.01)
(52) U.S. Cl. ............................................. 726/16; 726/26
(58) Field of Classification Search ........................ None
See application file for complete search history.

(56) References Cited

U.S. PATENT DOCUMENTS

| 6,026,502 A | 2/2000 | Wakayama |
| 6,958,691 B1 | 10/2005 | Anderson et al. |
| 7,277,752 B2 * | 10/2007 | Matos ............................... 607/5 |
| 2002/0032717 A1 | 3/2002 | Malan et al. |
| 2002/0133721 A1 | 9/2002 | Adjaoute |
| 2002/0184415 A1 * | 12/2002 | Naghavi et al. ................. 710/64 |
| 2004/0199790 A1 * | 10/2004 | Lingafelt et al. .............. 713/201 |
| 2005/0278784 A1 * | 12/2005 | Gupta et al. ..................... 726/23 |
| 2006/0021020 A1 * | 1/2006 | Coley et al. ..................... 726/11 |
| 2006/0095960 A1 * | 5/2006 | Arregoces et al. ............. 726/11 |

FOREIGN PATENT DOCUMENTS

| DE | 10251900 | 5/2004 |
| WO | WO03095024 A2 | 11/2003 |

OTHER PUBLICATIONS

Stallings, Willaim. Cryptography and Network Security. Third Edition.2003.*

* cited by examiner

*Primary Examiner* — Gilberto Barron, Jr.
*Assistant Examiner* — Venkat Perungavoor
(74) *Attorney, Agent, or Firm* — Lowe Graham Jones, PLLC

(57) ABSTRACT

Apparatus for interacting with a medical device which is suitable for connection into a communication network which comprises at least one insecure area and a secure area on the device side, wherein the apparatus comprises a transmission device for transmitting communication packets to and from the medical device via the communication network, it comprises a monitoring device for monitoring the state of the connection of the device to the network, and it comprises a breaker device for breaking an existing connection between the secure area and the insecure area of the network if, during the monitoring process, a state of the network connection is detected which poses a risk to a patient treated with the device or to the correct functioning of the device.

24 Claims, 18 Drawing Sheets

APPARATUS AND METHOD FOR PROTECTING A MEDICAL DEVICE AND A PATIENT TREATED WITH THIS DEVICE AGAINST HARMFUL INFLUENCES FROM A COMMUNICATION NETWORK

PRIORITY CLAIM

This application claims priority to German Application Serial Number 10 2006 026 088.0 filed Jun. 3, 2006 and German Application Serial Number 10 2007 024 720.8 filed May 25, 2007 and are hereby incorporated by reference.

FIELD OF THE INVENTION

The present invention relates to an apparatus for integration in a medical device which is suitable for connection into a communication network which comprises at least one insecure area and a secure area on the device side. The present invention also relates to a medical device per se, which is suitable for connection into a communication network comprising at least one insecure area and a secure area on the device side, and to a medical system comprising a plurality of such medical devices or sub-devices. The present invention also relates to a method for controlling a corresponding apparatus for integration in a medical device.

In the medical field, most devices have in the past been designed as stand-alone devices. Nowadays, however, an increasing number of these devices are incorporated in communication networks. The reason for this lies partly in an increasing cost awareness in medical establishments, which means that there is a need for improvement in the processes used, sometimes for central data storage and thus for the use of communication networks, but also in the growing complexity of medical devices which means that an implementation with a single computer system cannot be achieved or can be achieved only with great difficulty. Individual complex medical devices are therefore often de facto systems which are based on a number of individual computer sub-systems which are connected to one another via a communication network and contribute jointly to the overall functionality of the medical device. On the other hand, there are many systems composed of individual medical devices which provide an overall functionality only as a result of the interaction between the individual medical devices contained in the system, which functionality cannot be provided by the individual devices alone. These systems of medical devices are thus themselves medical devices which have a higher complexibility than the medical sub-systems/devices contained therein. For example, in the field of infusion pumps, considerable added value can be obtained if pumps can be joined together to form a pump system, within which the pumps communicate with one another. If such a pump system can also communicate with the outside world, this makes it possible to forward infusion data, obtained from the patients supplied with infusions by the pump system, to a hospital information system. It is then possible to regard the infusion pump system as a medical device within the meaning of the invention described here.

BACKGROUND

In recent years, in order to reduce costs, there has also been an increasing shift of patients from the in-patient to the out-patient sector. However, this can lead to a considerable reduction in costs only if the medical data obtained can be transmitted efficiently and in real time to the appropriate medical establishment for analysis and evaluation purposes. This also takes place increasingly with the aid of communication networks.

In this context, however, a large number of difficulties and sources of risk arise which are of high importance due to the high level of security that is necessary when treating patients and operating medical devices. By using communication networks in this sector, there is thus also a new type of risk to the patients and to the operators of medical devices. It is possible that the medical device will be violated by an influence coming from the communication network, in such a way that this may lead to a risk to the treated patient or to a malfunction of the medical device. Such an influence which may lead to a possible risk to the medical device will hereinafter be referred to as an attack on the medical device. Such an attack may for example be caused by software which deliberately attempts to exploit gaps in security to gain access to or falsify any confidential data of the computer system contained in the medical device, which may be used for criminal purposes. Such software will hereinafter be referred to as malware. Since malware corrupts the target parts of the functionality of a computer system in order to find or falsify the data, it must be assumed that there is a particularly high risk to the patient or to the correct functioning of the medical device if said computer system is attacked by malware.

In order to be able to ensure the data security and confidentiality of the data contained in the network, usually parts of the communication network with a different security level are assumed when designing communication networks. At the points of separation between these areas, usually security mechanisms such as firewalls for example are installed. However, the focus of such protection by the aforementioned security mechanisms lies in the protection of data security and confidentially, which is of particular interest commerciality, and is not adapted or is adapted only incompletely to the requirements stemming from medical devices.

It is even possible for there to be an attack on a medical device by other communication partners, i.e. usually medical devices within the part of a communication network that is regarded as secure, even though the individual communication partners are operating without faults and have a communication behaviour regarded as cooperative but which may expand when summed and in certain situations may lead to a malfunction. This is comparable to a traffic jam on a motorway, which arises spontaneously and without a perceptible external cause when the vehicle density reaches a certain level. Alternatively, there may be an attack on a medical device by other medical devices within the part of the communication network that is regarded as secure if the communication protocols of two classes of medical devices lead to possible misinterpretations or if the other medical device is overloaded by the communication of the medical devices.

The potential risk becomes particularly high when all-round software components, such as customary operating systems for example, are used to set up the medical device, which all-round software components have been developed for a number of possible applications, have a high inherent complexity and therefore are particularly susceptible to the risk of an attack. The manufacturer of a medical device is in a dilemma here since, on the one hand, the software component used poses a potential risk but, on the other hand, a development of the medical devices without the use of such components is so complex that this results in a high potential risk to the patient or to the correct functioning of the medical device. What makes the use of such software components even more risky is the fact that malware is usually written specifically for such software components and therefore exploits gaps in security therein in a targeted manner. The malware can pass into the medical device either indirectly via a connection of the secure part of the communication network to an insecure part, or else directly via data carriers, or a combination of both pathways.

SUMMARY

The object of the present invention is to eliminate or at least partially solve these difficulties and to provide an apparatus which makes it possible to protect medical devices against the aforementioned harmful influences from a communication network.

The present invention makes it possible to meet the specific requirements placed by medical devices on protection against attacks from the network or other malfunctions, and relates to an apparatus according to the preamble of claim 1, which comprises transmission means for transmitting communication packets to and from the medical device via the communication network, which comprises monitoring means for monitoring the state of the connection of the device to the network, and which comprises breaker means for breaking an existing connection between the secure area and the insecure area of the network if, during the monitoring process, a state of the network connection is detected which poses a risk to a patient treated with the device or to the correct functioning of the device. This has the advantage that, due to the particular requirements in the medical field and going beyond the customary properties of typical firewalls, in particular the connection of the secure area of the communication network to the insecure area can be completely cut if a risk of any type to the patient or the device is detected.

In one preferred embodiment of the apparatus according to the invention, the transmission means comprise a packet filter which carries out packet filtering on the communication packets transmitted between the insecure area and the secure area of the communication network, wherein the packet filter is suitable for blocking communication packets which pose a potential risk to the medical device. Furthermore, the breaker means may be formed by at least one breaker switch and the monitoring means may comprise at least one control logic which, when a state of the network connection which poses a risk to a patient or to the correct functioning of the device is detected, triggers opening of the breaker switch(es) so as to separate the insecure area from the secure area of the communication network which is connected directly to the medical device.

The aforementioned packet filter may be configured in such a way that it makes it possible to carry out bidirectional packet filtering on the communication packets transmitted between the insecure area and the secure area of the communication network. This therefore ensures control and filtering of the transmitted data in both directions. Moreover, in this case, the separation between the secure area and the insecure area of the communication network may preferably be implemented as logical segmentation.

As a result, the packet filter may in particular partially or completely replace the aforementioned monitoring means and/or the breaker means by blocking harmful communication packets or all communication packets during the filtering process.

However, the separation between the secure area and the insecure area of the communication network may also be implemented as physical segmentation, in particular in the form of different physical transmission paths in the secure area and in the insecure area of the network or by different instances of the same transmission path in this area. If the transmission paths used in the communication network are cable-based, it is particularly advantageous to use optical fibres for the transmission paths, as will be illustrated and explained in more detail in the following description.

In a further embodiment of the present apparatus, said control logic has means for carrying out a static and/or dynamic check of the data to be transmitted in the communication network, the result of which check leads to an existing connection between the insecure area and the secure area of the network being maintained or cut by triggering the breaker switch(es).

The aforementioned breaker switch may be located on the side connected to the secure area of the communication network and/or on the side of the apparatus according to the invention connected to the insecure area of the communication network. As a result, it is possible to separate only the medical device and/or both the medical device and the apparatus itself from the insecure area of the network.

In one particularly advantageous embodiment of an apparatus according to the invention, said apparatus comprises a redundant architecture by integrating in the monitoring means a model of the functions of the transmission means which makes it possible to check the correct functioning thereof. An apparatus according to the invention may also comprise at least two diversitary channels, each with their own transmission means, monitoring means and breaker means, wherein each channel can monitor both itself and also the other channel independently and can separate from the insecure area of the communication network when a state of the network connection which poses a risk to the patient or to the correct functioning of the device is detected. The two aforementioned embodiments of an apparatus according to the invention are characterised by a particularly high level of security against attacks from the insecure area of the communication network or other malfunctions.

The present invention also relates to a medical device per se, which is suitable for connection into a communication network which comprises at least one insecure area and a secure area on the device side, and which comprises an apparatus according to the invention in one of the embodiments mentioned above. The medical device may in particular comprise infusion pumps or patient monitors.

The present invention also relates to medical systems comprising a plurality of medical devices of the aforementioned type or such sub-devices, wherein the system comprises at least one apparatus according to the invention as mentioned above.

Finally, the present invention relates to a method for controlling such an apparatus, wherein the method ensures the transmission of communication packets to and from the medical device via the communication network, it monitors the state of the connection of the device to the network, and it breaks an existing connection between the secure area and the insecure area of the network if, during the monitoring process, a state of the network connection is detected which poses a risk to the patient or to the correct functioning of the device. The various embodiments and advantages of such a method will be explained in detail in the following description.

BRIEF DESCRIPTION OF THE DRAWINGS

The appended figures show by way of example a number of embodiments of an apparatus according to the invention, of a medical device or system according to the invention, and of a method according to the invention.

DETAILED DESCRIPTION OF THE INVENTION

Figure 1:
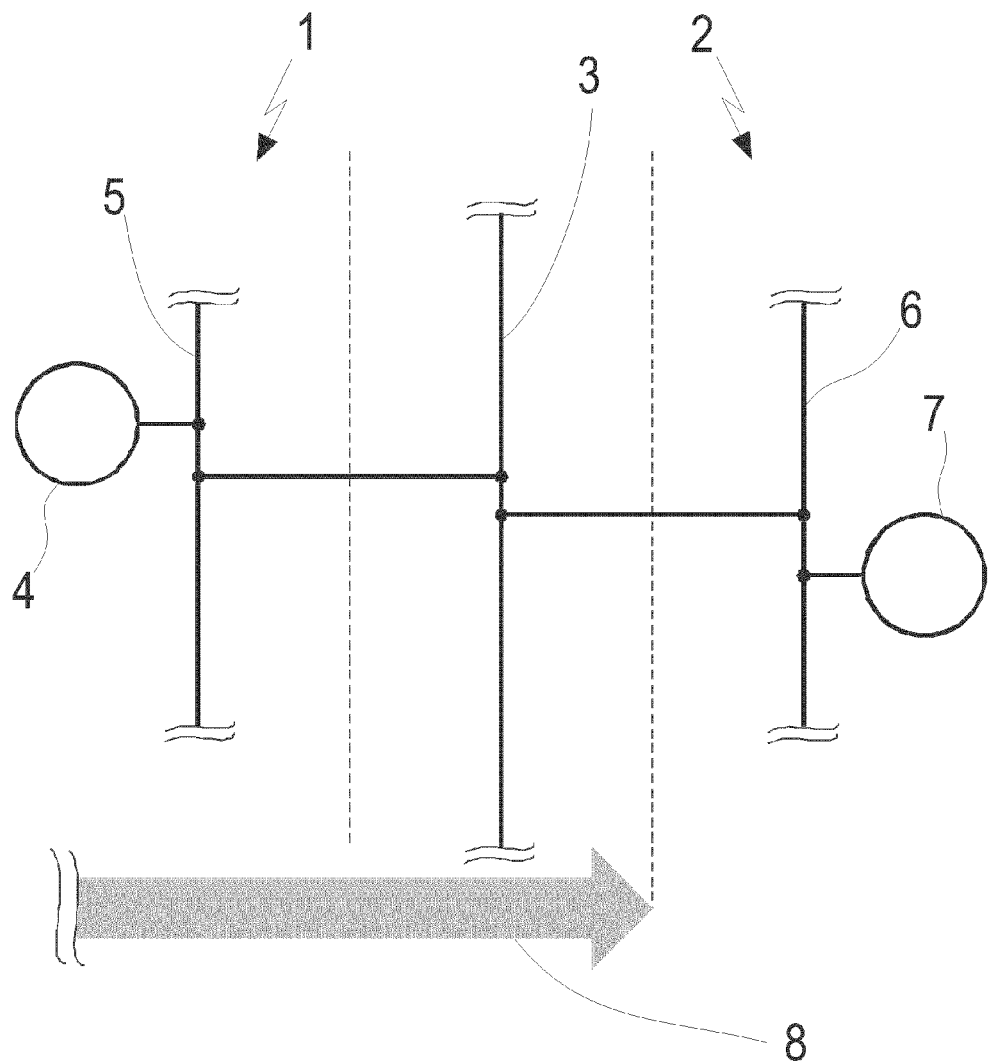
FIG. 1 shows the connection, in a patient's home, of a medical device located in the patient's home, said connection being customary in the prior art.

Hereinbelow, the present invention will now be explained in detail with reference to the above figures. Firstly, reference is made to FIG. 1, which shows the connection which has to date been customary of a data-acquiring medical device which is located in the patient's home. Here, the patient's home 1 and the medical establishment 2, the system boundaries of which are indicated in dashed line, are connected to one another via a WAN network 3, e.g. the Internet. The data-acquiring medical device 4 is coupled to the WAN network 3 via the LAN network 5. The LAN network 6 of the medical establishment is coupled thereto and to that of the evaluating medical device 7. The area 8 of the communication network which is insecure from the point of view of the medical establishment is symbolised by a grey arrow in FIG. 1. The object of the present invention is to protect the medical device located in the secure area of the communication network against influences from the insecure area 8 of the network. This should be achieved in a simple and efficient manner and should nevertheless meet the high security standards customary in the medical sector.

Figure 2:
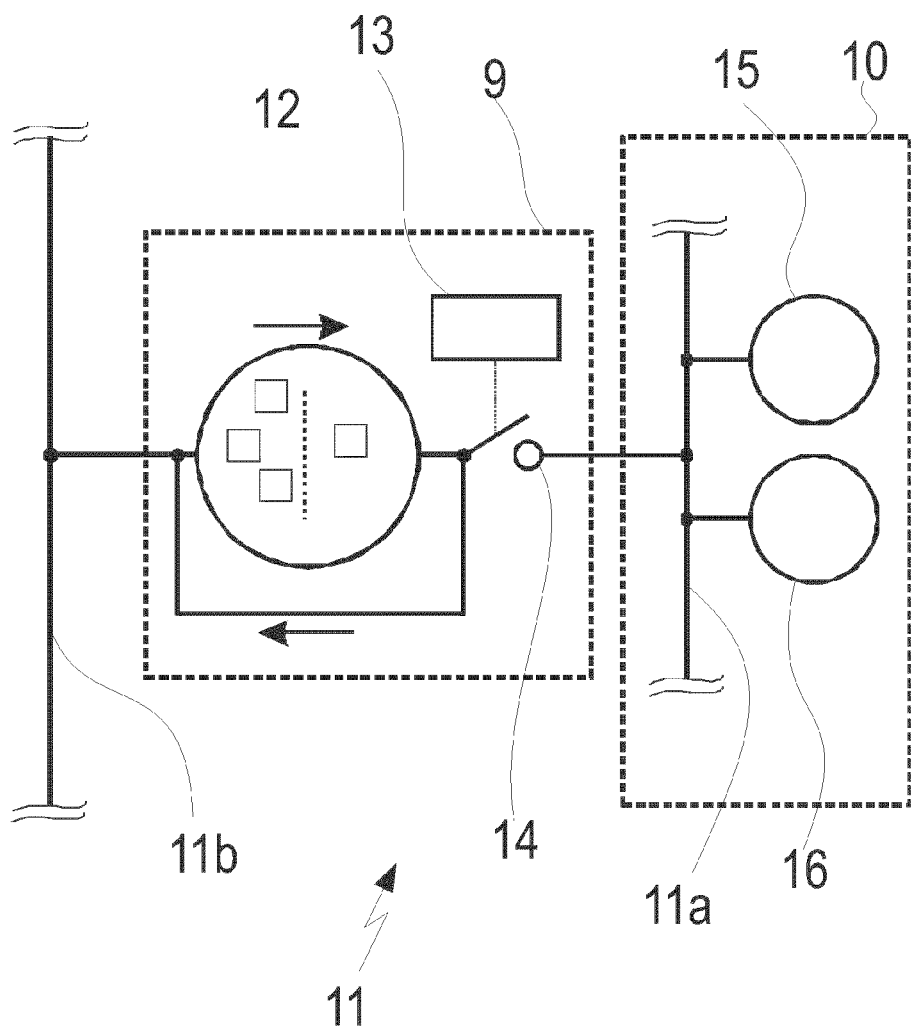
FIG. 2 illustrates schematically and by way of example the principle of an apparatus according to the invention.

FIG. 2 shows a schematic diagram of the apparatus according to the invention. The apparatus 9 (i.e., transmission means) according to the invention protects a medical device 10 against possible attacks which may come from the insecure area 11b of the communication. network 11. To this end, it operates a packet filter 12 (i.e., a monitor means) on the path from the insecure part of the communication network 11 to the medical device, which packet filter blocks the communication packets which pose a potential risk to the medical device 10. A control logic 13 makes it possible to separate the insecure area 11b of the communication network 11 from the medical device 10 by means of a breaker switch 14 (i.e., a breaker means). A form of separation in which the apparatus according to the invention can also separate itself from the secure area 11a of the communication network 11 is shown here by way of example.

The medical device 10 may optionally be designed as a system comprising a plurality of medical sub-devices 15, 16 which are connected to a secure area 11a of the communication network 11.

Figure 3:
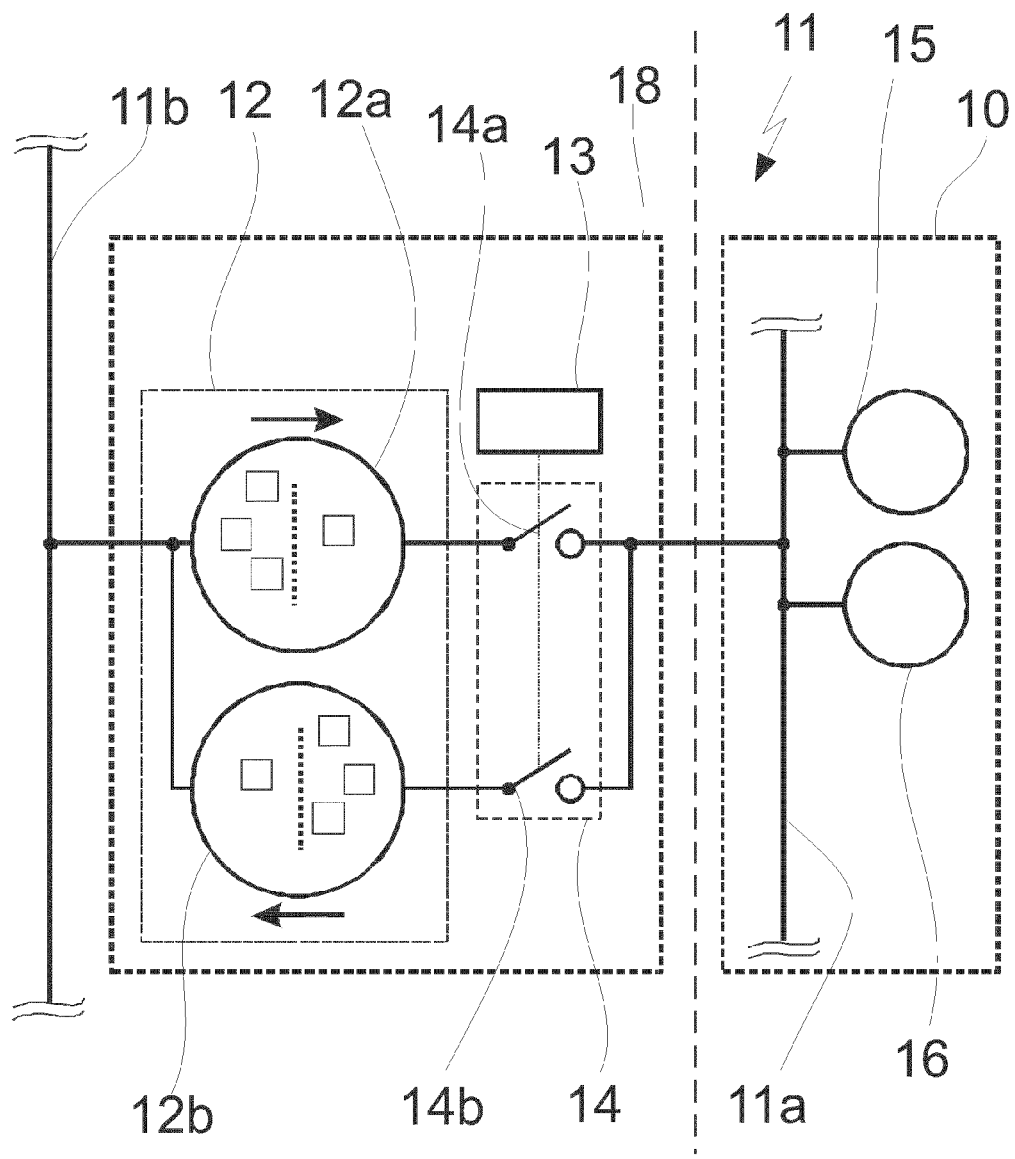
FIG. 3 shows an apparatus according to the invention with bidirectional packet filtering in one example of embodiment.

The apparatus according to the invention may advantageously be configured to carry out the packet filtering in a bidirectional manner, that is to say both in the direction from the insecure area 11b to the secure area 11a of the communication network 11 and in the opposite direction. In this case, not only is the medical device protected against an attack which may come from the insecure part of the communication network 11, but also the influence exerted by the medical device on this insecure part of the communication network 11 in the event of malfunction is minimised. FIG. 3 shows the schematic diagram of an apparatus according to the invention with bidirectional packet filtering.

The apparatus according to the invention with bidirectional packet filtering 18 protects a medical device 10 against possible attacks which may come from the insecure area 11b of the communication network 11, and at the same time ensures that, in the event of a malfunction, there is minimal loading of the insecure part 11 of the communication network 11 by the medical device 10. To this end, it operates a packet filter 12 which is composed of two packet filters which monitor the different directions of packet flow. On the path from the insecure part of the communication network 11 to the medical device, a packet filter 12a is used which blocks communication packets which may pose a potential risk to the medical device 10. In the opposite direction, a packet filter 12b is used which can minimise the back-effect of the medical device on the insecure part of the communication network 11. A control logic 13 makes it possible to separate the apparatus 9 itself and the insecure area 11b of the communication network 11 from the medical device 10 by means of the breaker switch 14, wherein the latter is composed of two parts 14a and 14b for the different directions of communication flow. The two parts of the breaker switch are normally actuated at the same time, but alternate switching may also be useful in special cases, e.g. to minimise the load on the communication network 11.

The medical device 10 may also optionally be designed here as a system comprising a plurality of medical sub-devices 15, 16 which are connected to the secure area 11a of the communication network 11.

A complete separation of the medical device 10 from the insecure area 11b of the communication network 11 carried out by the breaker switch 14, or a partial separation carried out by the packet filter 13 (since communication packets fail to appear), must be considered within the context of the risk analysis of the medical device 10 and must lead to a secure state thereof by ruling out any particular risk to the operator or patient of the medical device 10 in order to be able to use the apparatus 9 according to the invention. In practice, this restriction of use of the apparatus 9 according to the invention should barely be relevant, since a break in a network connection caused e.g. by faults in the wiring should always be taken into account, and other methods for minimising risk, such as e.g. redundant network architectures, are too expensive in most use cases.

In order that the packet filter 12 and the breaker switch 14 can carry out their tasks, segmentation must take place, i.e. a logical and/or physical separation between the insecure area 11b and the secure area 11a of the communication network 11. Otherwise, communication packets could be transported at will between the insecure area 11b and the secure area 11a of the communication network 11, without being able to be acted upon or influenced by the packet filter 12 and breaker switch 14.

The way in which segmentation of the two parts 11 and 17 of the communication network 11 is carried out by an apparatus according to the invention may be completely different. Examples of possible types of segmentation include the use of communication networks 11 based on different physical principles (e.g. LAN/WAN), a different protocol, the transport of files or the conversion of TCP/IP packets, but other types of segmentation are also conceivable.

The functioning of the breaker switch 14 depends essentially on the type of segmentation used between the insecure area 11b and the secure area 11a of the communication network 11.

If an apparatus according to the invention with bidirectional packet filtering 18 is used, the segmentation between the secure area 11a and the insecure area 11b of the communication network 11 may take place logically, e.g. by using a different communication protocol on the communication network 11 behind the apparatus 18 according to the invention than in front of the apparatus according to the invention. In the normal case, the packet filter 12—which in any case carries out the protocol analysis—also carries out a translation between the different communication protocols.

The packet filter 12a can then e.g. if necessary not carry out the protocol translation for communication packets that are to be filtered out. As a result, no more valid translated communication packets are produced e.g. in the secure area 11a of the communication network 11 for the corresponding communication packets. It is even conceivable that, in this case, the function of the breaker switch 14 is carried out by the packet filter 12a by the latter adjusting the translation permanently and for all communication packets. The medical device 10 is then logically separated from the insecure area 11b of the communication network 11, even though no physical separation has taken place. The packet filter 12b must carry out the corresponding tasks in the opposite direction, and the same principles apply in the opposite direction. In this way, a very cost-effective structure of the apparatus according to the invention can be achieved.

However, it is also conceivable in theory that communication packets of the communication protocol used in the insecure area 11b of the communication network 11 are also valid communication packets in the communication protocol used in the secure area 11a of the communication network 11 and carry out attacks on the medical device 10. Although this risk can be minimised by careful selection of the communication protocols used, a certain level of risk will nevertheless remain if an attack on the secure area 11a of the communication network 11 takes place by means of a "brute force attack" or a "bubbling idiot" which transmits random communication packets. In this case, after a certain period of time, valid communication sequences for the communication protocol used on the secure area 11a of the communication network 11 will be "guessed".

A particularly high level of protection of the medical device 10 can therefore be achieved if there is physical segmentation between the insecure area 11b and the secure area 11a of the communication network 11.

Such a physical segmentation can be achieved by using different physical transmission paths for the insecure area 11b and the secure area 11a of the communication network 11. For example, the insecure area 11b of the communication network 11 could use radio-based transmission while the secure area 11a uses transmission via network cables. However, different instances of the same transmission path can also be used, for example by using two separate network cables or different radio carrier frequencies for the two areas 11a and 11b of the communication network 11.

However, one particularly advantageous use of the described device 9 is achieved in the case of cable-based electrical communication networks 11 when a physical segmentation of the two areas 11a and 11b of the communication network 11 is carried out. In this case, the described apparatus can also protect the medical devices against electrical interference, which may be introduced into the medical device through the insecure area 11b of the communication network 11 and may give rise to a malfunction thereof and thus a risk to the patient or user.

The protection of contact voltages against abnormally high voltages in the insecure area 11b of the communication network, which is important for medical devices, can in this case also be carried out by the apparatus 9 according to the invention.

If protection of the contact voltages is particularly critical for the given intended use, it may be advantageous to use a communication network 11 based on optical fibres for the secure area 11a of the communication network 11, since in principle no potential equalisations take place through such a network.

Both the insecure area 11b of the communication network 11 and the secure area 11a of the communication network 11 may be cable-based. However, other embodiments which transmit the data via light, radio, sound or other transport paths are also conceivable. The methods of transmission must not be the same in both areas 11a and 11b of the communication network 11; in this case, it is advantageous if the apparatus according to the invention can itself carry out a conversion between these transmission methods, since then no other device is required for this conversion.

Figure 4:
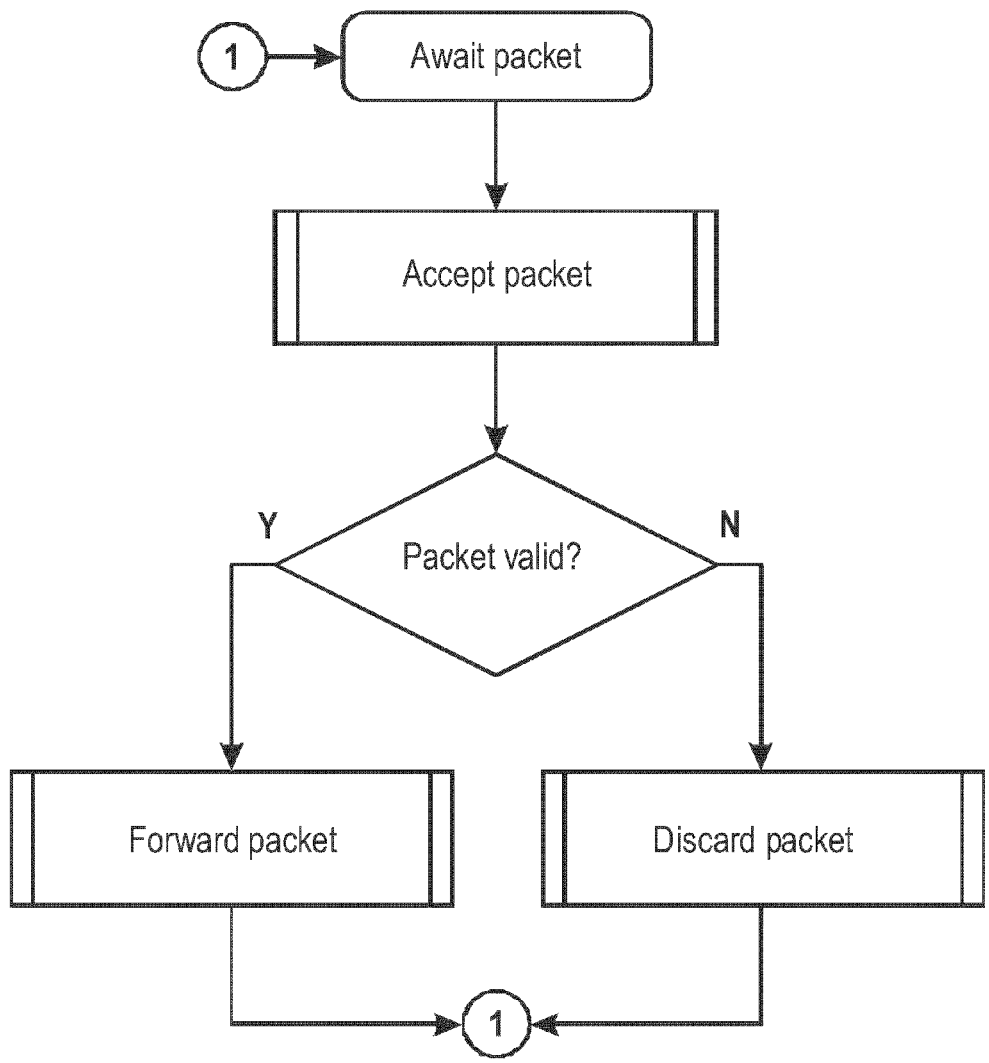
FIG. 4 shows schematically the algorithm of a packet filter used in an apparatus according to the invention.

FIG. 4 shows a simple possible basic algorithm for the packet filter 12. The packet filter waits to receive communication packets from the insecure area 11b of the communication network 11. As soon as a communication packet is present, it accepts said packet and then checks whether the packet is valid for forwarding to the medical device 10. If this is the case, the communication packet is forwarded; if not, it is discarded. The packet filter 12 then waits to receive the next packet.

It may be advantageous here, in particular so as to be able to track the behaviour of the apparatus 9 according to the invention, if a logging of received and discarded communication packets can be carried out and thus the correct configuration of the packet filter 12 can be checked.

In order to be able to decide which communication packets should be taken over from the insecure area 11b of the communication network 11 to the secure area 11a of the communication network 11, the packet filter 12 evaluates additional knowledge about the structure of the medical establishment, the internal structure of the medical device and of its sub-devices, its properties, present state and the like.

In the simplest case, e.g. only the communication packets coming from fixed MAC addresses or IP addresses can pass the packet filter 12, or only those which carry out communication on permitted ports. Further checks of the communication, such as a stateful inspection, may also be carried out. The behaviour of the apparatus 9 according to the invention at the stage of monitoring the network connections would in this case be similar to that of a hardware firewall; however, the rules for packet filtering could be specified much more accurately and adapted to the medical device to be protected. Unlike customary firewalls, however, here the connection to the insecure area 11*b* of the network 11 is cut when harmful communication packets are detected.

It is moreover particularly advantageous if the apparatus 9 according to the invention carries out a protocol analysis of the communication protocol to be transmitted to the medical device 10, and allows through the packet filter 12 only those communication packets which correspond to the communication protocol of the medical device 10. As a result, the risk of an attack on the medical device 10 is already considerably reduced.

Furthermore, a protocol analysis also makes it possible to check data occurring within the protocol for valid data values, and to allow through the packet filter 12 only those communication packets whose data lie within the permitted value range.

Unlike firewalls, which protect communication networks 11 for general-use computer systems, the packet filter 12 can be adapted precisely to the communication protocols to be used, since the installation of any programs on the computer systems embedded in medical devices is usually neither possible nor permitted by the manufacturer if a possible risk to the operator or patient of the medical device is posed by these devices. Therefore, the communication protocols used by a medical device undergo changes that might require adaptation of the packet filter more rarely than is the case with computer systems for general use.

One particularly advantageous embodiment of the apparatus 18 according to the invention with bidirectional packet filtering is obtained when a check that is carried out on the communication protocols used is also at the same time used to convert the data into communication protocols used by other medical devices and/or into a communication network 11 based on different physical principles, and thus to allow devices which are in fact incompatible to communicate with one another.

Furthermore, in order to be able to decide when a separation from the potentially insecure part of the communication network 11 should be carried out, additional knowledge about the structure of the medical establishment, the internal structure of the medical device(s), the properties thereof and the like is evaluated.

Moreover, in the case of a detected potential risk posed by the insecure area 11*b* of the communication network 11, the described apparatus can completely break the connection thereof to the medical device 10, so that it is possible to restrict some of its functions but its core functionality is still provided.

Figure 5:
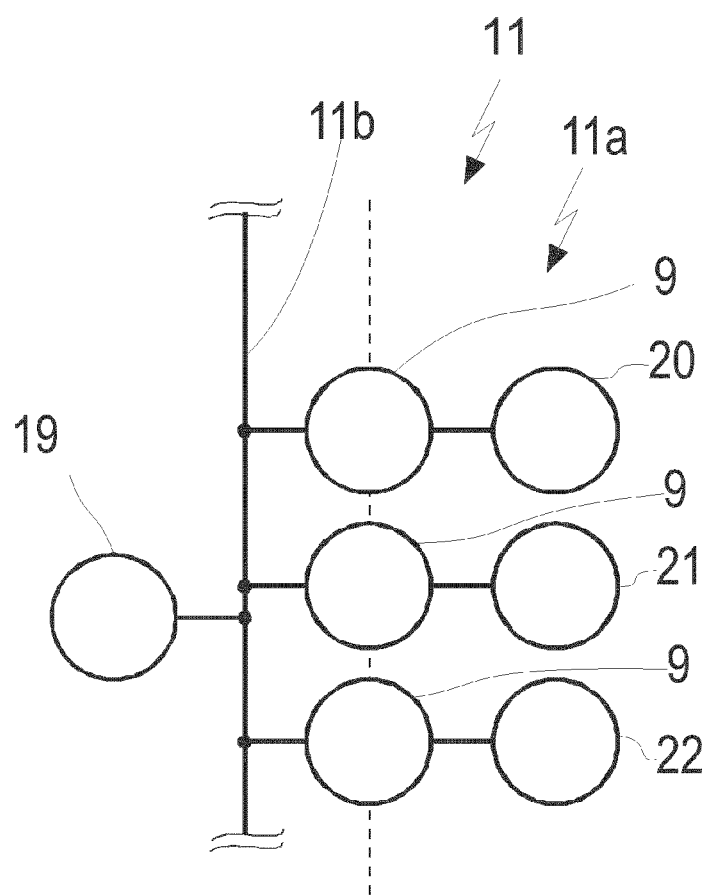
FIG. 5 shows the separation of patient monitors from a central system.

Such a separation will be explained on the basis of the example of a patient monitor system, which is shown schematically in FIG. 5. A central system 19, which is located in the insecure area 11*b* of the communication network 11, is connected to a plurality of patient monitors 20, 21 and 22 protected by apparatuses 9 according to the invention, each of said patient monitors thus being located in a secure area 11*a* of the communication network 11. In the case of a detected potential risk, the connection to the insecure area 11*b* of the communication network 11 and thus to the central system 19 can be broken by the apparatuses 9 according to the invention, which restricts the functionality of the patient monitors 20, 21 and 22, but the core functionality thereof (the monitoring function) continues to be provided, albeit in a less convenient manner. During the time the connection is broken, the patient monitors 20, 21 and 22 are unable to access the central system 19, and vice versa.

Such a separation may be very advantageous in particular when e.g. older medical devices are used which are only inadequately prepared for the high data rates found in present-day communication networks 11, since dedicated communication networks 11 were assumed during development of the device even for these devices, but this prerequisite is no longer given due to the infrastructure of the medical establishment. If e.g. complicated interrupt treatment routines are used in the medical devices, in some circumstances even a simple overload on the communication network 11 may cause an inadmissibly high load on the processors in the medical devices, even if the actual data transmitted is entirely harmless. While an individual medical device must in this case pass into a secure state, the simultaneous passing of a relatively large group of medical devices into this state may cause a critical overall state brought about by the complexity of the group. If, for example, an individual patient monitor in an intensive care unit has a fault, but the latter detects this itself and transmits an alarm to the staff by virtue of a device alarm, this situation per se need not necessarily be classified as critical. The same applies in respect of one infusion pump. However, if all patient monitors and all infusion pumps in the same intensive care unit fail at the same time on account of malfunctions provoked by the communication network 11, the resulting risk to all the patients treated in said unit is much greater.

The control logic 13 can make the decision to carry out a separation of the areas of the communication network 11 based on static checks of the data to be transmitted. Such checks may include for example a check of IP addresses of the communication partners, the MAC addresses used by the latter, a use of certain ports and/or in particular a syntax and/or semantics and consistency check of the transmitted data.

In the normal case, a static check of communication packets to be transmitted will more often lead to a discarding of the packets in the packet filter than to a separation from the insecure area 11*b* of the communication network 11. However, in the case of particularly high security requirements for the medical device 10, it may be useful if excessively frequent failures of the static validity checks lead to a temporary or even permanent separation from the insecure area 11*b* of the communication network 11.

A decision to carry out a separation of the areas 11*a* and 11*b* of the communication network 11 may however also take place by carrying out a dynamic check of the data to be transmitted. Such checks may for example be the response times of the communication partner, a maximum permissible data flow to the medical devices to be protected or else a minimal data flow which indicates correct functioning of the communication partner. State-based monitoring processes, which include a model of the devices involved in the communication, are also very advantageous here.

One particular type of use of the device 9 according to the invention is obtained when a plurality of medical sub-devices, which work together as one medical system/device, are connected to one another through an insecure part 11*b* of the communication network 11. In this constellation, it is recommended to equip the medical (sub-)devices in each case individually with apparatuses 9 according to the invention. In this case, it may be even more useful to use apparatuses 18 according to the invention with bidirectional packet filtering, as will be demonstrated later.

Figure 6:
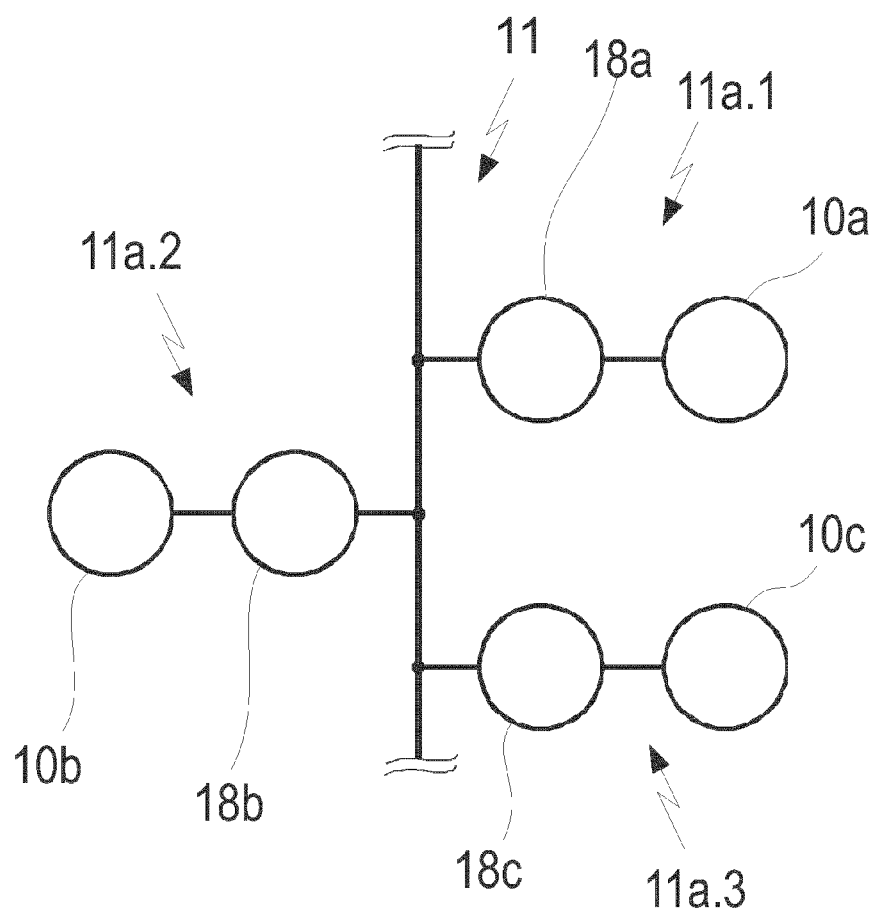
FIG. 6 shows by way of example the structure of a system of medical devices which are connected to one another through an insecure part of a communication network.

FIG. 6 shows the structure of a system of medical devices which are connected to one another through an insecure part of the communication network 11. The two medical devices 10a and 10b, which together form a medical system, are connected to one another via the insecure area 11b of the communication network 11. They respectively form part of secure areas 11a.1 and 11b.2 of the communication network 11, which are protected by the apparatuses according to the invention with bidirectional packet filtering 18a and 18b. A further medical device 10c which does not form part of the aforementioned medical system is protected by its assigned apparatus 18c according to the invention and is connected to the insecure area 11b of the communication network 11.

If the packet filters of the apparatuses 18a, 18b and 18c according to the invention are optimally set and if a suitable communication protocol is used, a communication can take place between the medical devices 10a and 10b without this being perceived by the medical device 10c. Conversely, a communication can take place between the medical device 10c and other devices located in the insecure area of the communication network 11 without this affecting the medical devices 10a and 10b. However, if the communication protocols used by the devices 10a, 10b and 10c are the same, and if e.g. part of the communication is carried out as a broadcast—i.e. if it addresses all the participants in the communication network 11 simultaneously—the abovementioned method may fail.

Figure 7:
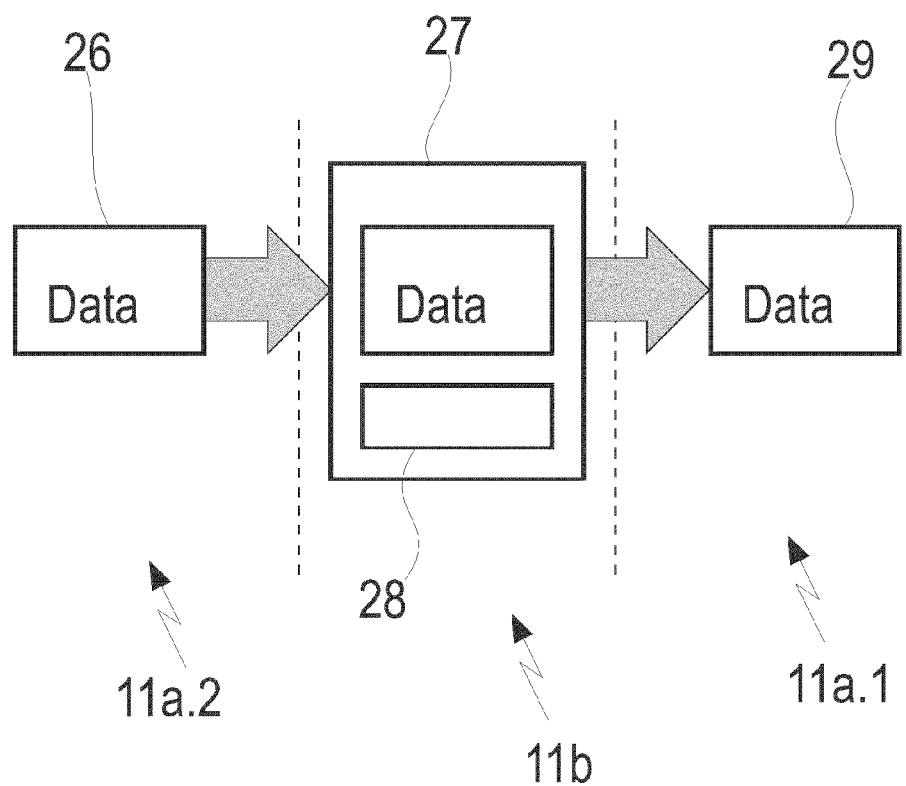
FIG. 7 illustrates the use of modified communication packets in the insecure part of the communication network.

In this case, it is recommended if the packet filters 13 of the apparatuses 10a and 10b according to the invention which are assigned to the medical devices 18a and 18b carry out a translation of the communication protocols in such a way that communication packets which are modified with respect to the original protocol are used in the insecure area 11b of the communication network 11. FIG. 7 schematically shows the course of such a procedure with reference to FIG. 6.

At the transition from a secure area 11a.2 of the communication network 11, a communication packet 26 which contains the data denoted "Data" is converted by the apparatus 18b according to the invention into a different communication packet 27 which is transported within the insecure area 11b of the communication network 11. The conversion may take place very easily and quickly by embedding the original communication packet 26 in another communication packet 27. It may be advantageous here if additional data 28—such as a signature for example—are embedded in the communication packet 27, e.g. in the case of identical protocols to separate different groups of medical devices from one another and/or to be able to ascertain as the apparatus 18a according to the invention that the data have not been altered within the insecure part 11b of the communication network 11. When forwarding it, the device 18a according to the invention converts the modified communication packet 27 into a communication packet 29 which can be used by the medical device 10a and which, if the same communication protocol is used, should usually be identical to the original communication packet 26.

In this way, it is possible in an efficient manner to reduce the mutual influencing of different communication to an absolute minimum. If it is ascertained by the device 18a according to the invention, e.g. by checking the signature, that the incoming communication packet 27 has been falsified, the corresponding packet 29 is not generated. There is then possibly an indication of an attack and the control logic 13 might carry out the separation from the insecure part of the network—optionally also only after such events have occurred more frequently.

Figure 8:
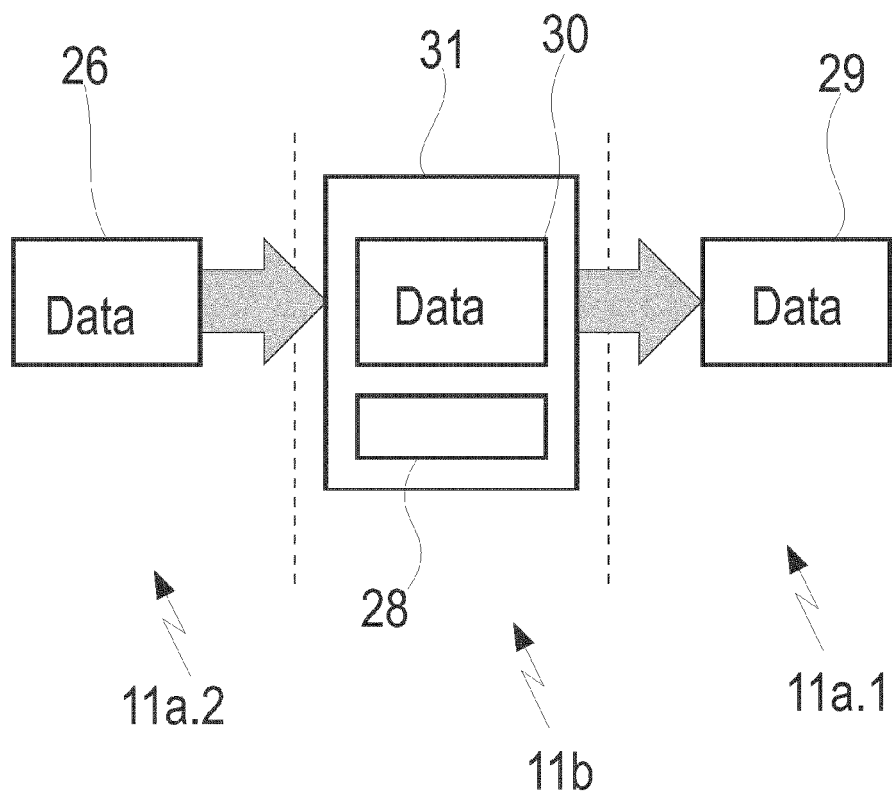
FIG. 8 shows the use of encrypted communication packets in the insecure part of the communication network.

However, with the described network structure in which the insecure area 11b of the communication network 11 is used in order to allow two medical sub-devices to communicate with one another, in addition to the potential risks to the patient and/or operator as described above there are also requirements placed on the security of data with respect to visibility to unauthorised third parties. These requirements can be met by expanding the procedure shown in FIG. 7. FIG. 8 shows the course of this expanded procedure.

A communication packet 26 contains the data denoted "Data". At the transition from a secure part 11a.1 of the communication network 11 to the insecure area 11b, it is converted by the apparatus 18b according to the invention into a different, modified communication packet 31. Unlike the procedure in FIG. 7, the original communication packet is not simply embedded in the new communication packet but rather the data region is converted into an encrypted data region 30 which is denoted "dATA". Here, the symmetrical and/or unsymmetrical methods known from other fields of application may be used, optionally with an additionally embedded signature in order to distinguish between different groups of medical devices or for a quick check of the integrity of the communication packets. At the transition to the second secure part 11a.2 of the communication network 11, the modified and encrypted communication packet 31 is converted into a communication packet 29 which can be used by the medical device 23, which if the same communication protocol is used is usually identical to the original communication packet 26.

As a result, a type of virtual private network (VPN) is obtained between the devices 10a and 10b, so that contents of the communication cannot be perceived, modified or read by other communication-capable devices in the insecure area 11b of the communication network 11. This procedure is particularly advantageous when the insecure area 11b of the communication network 11 is the Internet, as would usually be the case in the connection of a medical device within the patient's home.

This security can be used in a very advantageous manner even within a medical establishment for transporting data through a "public part" of the communication network 11, without giving unauthorised persons the possibility of seeing the data. If a very detailed analysis of the transmitted data is carried out for security purposes, the described invention can in a particularly efficient manner separate the data into a non-encrypted "public" part and an encrypted "private" part.

If data are to be exchanged between medical sub-devices 10a and 10b which have a particularly high potential risk for possible falsification, it may be advantageous to prevent such possible falsification in the insecure area 11b of the communication network 11 by storing and transmitting "obsolete" communication packets in that, contained in each communication packet transmitted via the insecure area 11b of the communication network 11 is a variable part whose correctness is checked upon receipt, before the communication packet passes through the packet filter. This may be for example a simple number having a defined sequence. If a clock time is used as the variable part, it can even be checked whether the packet is still valid or has already taken too long to be transported in the communication network 11.

If one of the medical sub-devices 10a and 10b requires a particular reaction when terminating the communication with the respective other medical sub-device, but the communication does not adhere to any fixed time pattern, the associated apparatuses 18*a* and 18*b* according to the invention can transmit signs of life at fixed time intervals in order to be able to check the functioning of the communication. If these signs of life stop, then a message must be sent in a suitable manner to the corresponding device 10*a* or 10*b* to be monitored, e.g. via the generation of a suitable communication packet or else by using dedicated control lines.

In the case of even higher requirements placed on the manipulation security of data to be transmitted, the transmitting apparatus 18*a* or 18*b* according to the invention can transmit with each relevant communication packet a transaction number (TAN), on the basis of which the receiving apparatus 18*b* or 18*a* according to the invention can determine without doubt the origin of the communication packet. A list of TANs must then have been transmitted to both apparatuses 18*a* and 18*b* according to the invention beforehand via a different, secure route—e.g. by means of data carriers. With each TAN transmitted to the respective communication partner, said TAN must be scored off the list by the two apparatuses 18*a* and 18*b* according to the invention.

Another way of hiding data which are transmitted in the insecure area 11*b* of the communication network 11 may take place by issuing addresses in the protected part of the communication network 11 which are not known to the outside. Any possible influences from the potentially insecure communication network 11 are thus made much more difficult.

Due to the functioning of the described apparatus, the latter can also very advantageously perform further tasks which to date have been carried out by special devices. For example, it is possible without much additional complexity to integrate a virus scanner into the device, which checks all the data traffic for the presence of computer viruses.

The described apparatus may also carry out a caching of data to be transmitted via the communication protocol, i.e. it may buffer-store said data at all times or only for the duration of a separation from the potentially insecure area 11*b* of the communication network 11, in order to transmit them automatically to the communication partner once the connection has been successfully re-established.

It may carry out proxying and thus may send back to a device, which should be a device connected to a serial interface with the correspondingly fast response times, during a protocol translation and connection via the Internet with correspondingly slow response times, confirmations for receipt of packets, and only when these signals are stopped for a relatively long time may place the device to be protected into a mode in which the connection is considered to be cut.

Other possible tasks which can advantageously be performed by the described device include e.g. access control for data in the secure communication network 11, or even the protection of software licences in the communication network 11.

However, due to the direct contact with the insecure area 11*b* of the communication network 11, there is the risk that the described device will itself be disrupted in its functioning by an attack from the communication network 11, and therefore cannot perform its protection function or can perform said protection function only to a limited extent.

Figure 9:
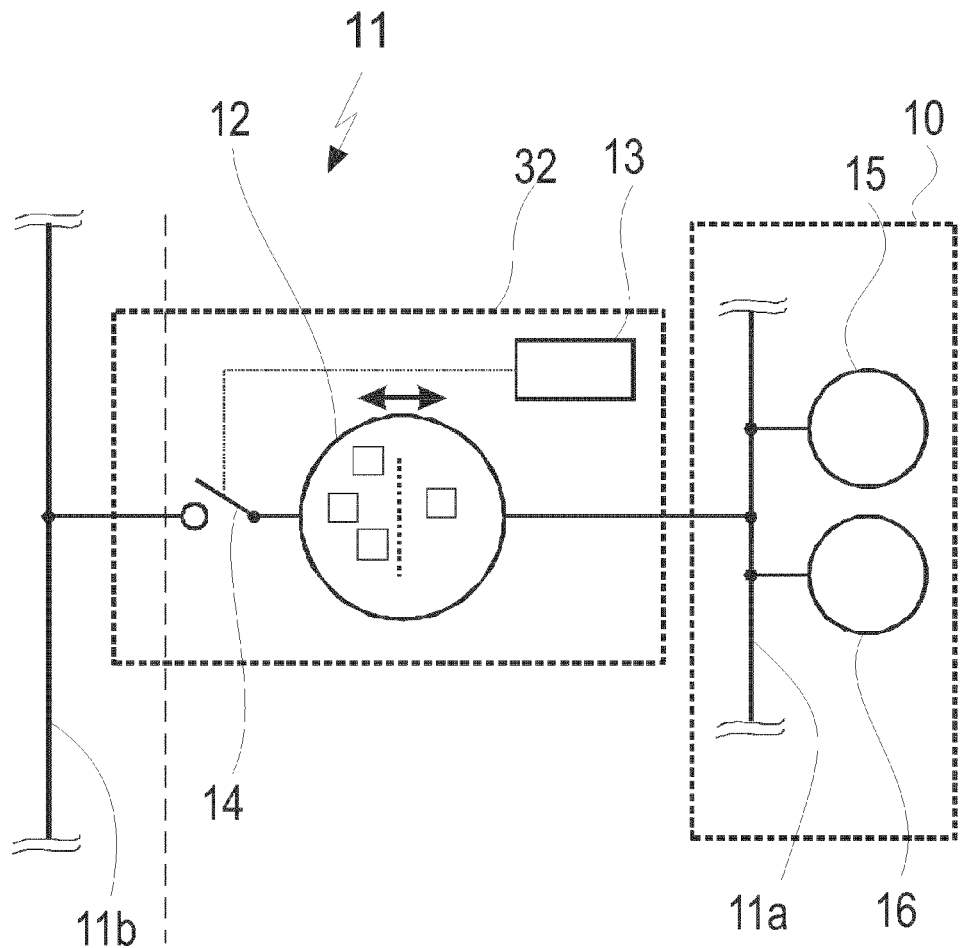
FIG. 9 shows a configuration in which the apparatus according to the invention can be separated from the insecure part of the communication network.

It may therefore be useful if the apparatus according to the invention can separate itself from the insecure area 11*b* of the communication network 11, by means of the breaker switch, when the control logic 13 detects a potential attack on the medical device or the device according to the invention. FIG. 9 shows the schematic structure of an apparatus according to the invention which is configured in this way.

The packet filtering 12 is designed to be bidirectional here by way of example; however, unidirectional packet filtering, as shown in FIG. 2, is also conceivable. In the apparatus 32 according to the invention, the breaker switch 14 is located on the side which is connected to the insecure area 11*b* of the communication network 11. The control logic 13 can thus separate the device 32 according to the invention together with the medical device 10 from the insecure area 11*b* of the communication network 11.

Due to the complete separation from the insecure area 11*b* of the communication network 11, no further attack on the apparatus 32 according to the invention is possible. The state of separation from the insecure area 11*b* of the communication network 11 must be the secure state for the medical device 10 and is to be assumed e.g. also in the event of failure of the supply voltage of the device 32 according to the invention.

It may be a useful expansion of the concept if the security logic 13 has the possibility of carrying out a reset and, associated therewith, a restart of the apparatus 32 according to the invention so that it is ensured that the apparatus is placed in a defined, correct starting state once a potential attack on the apparatus according to the invention has been deflected by opening the breaker switch 14.

An even more critical situation might arise if the device 9 according to the invention, due to a malfunction, itself carries out an attack on the medical device 10 to be protected. It is therefore advantageous, as shown in FIG. 2, if the control logic 13 separates the apparatus 9 according to the invention together with the insecure area 11*b* of the communication network 11 from the secure area 11*a* of the communication network 11 by means of the breaker switch 14 as soon as a restriction of the functioning of the device 9 according to the invention is detected. Accordingly, the safe state of the apparatus 9 according to the invention is understood to be an opening of the breaker switch 14 and thus the separation of the insecure part 11 and of the apparatus 9 according to the invention from the secure area 11*a* of the network. This state is therefore to be assumed e.g. also in the event of failure of the supply voltage of the apparatus 9 according to the invention.

Figure 10:
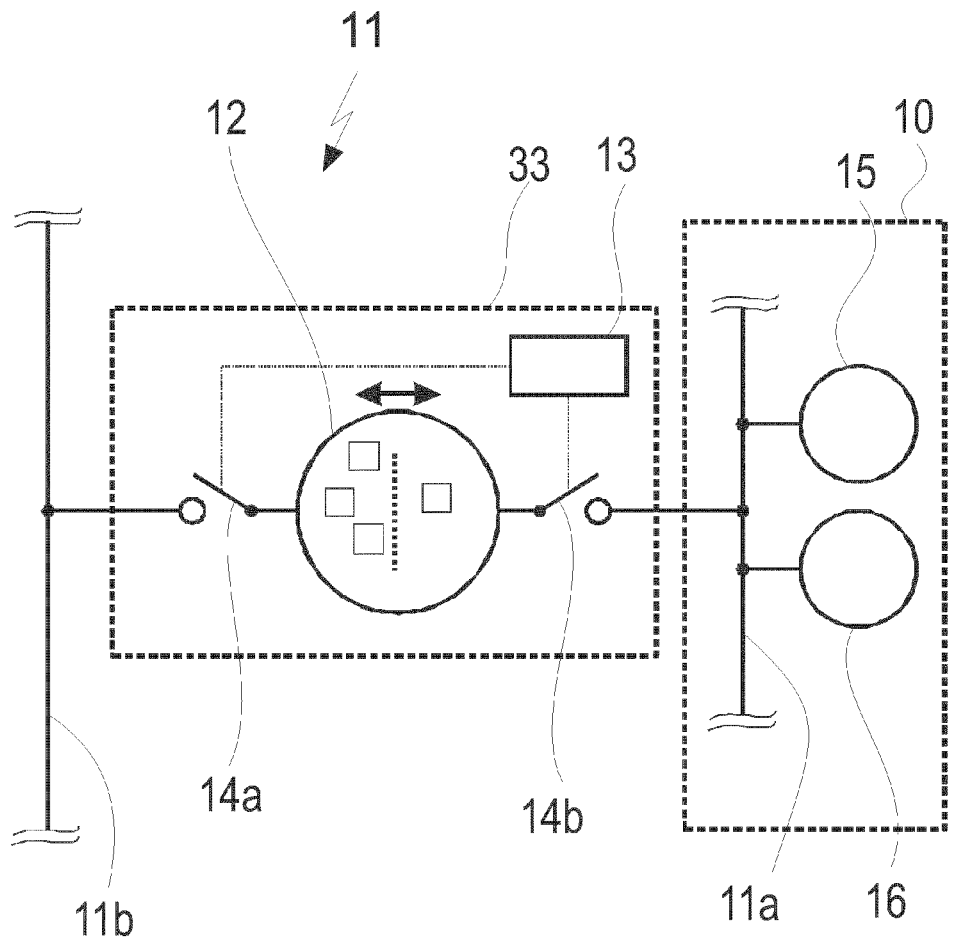
FIG. 10 illustrates a configuration which allows separation of the apparatus according to the invention on both sides.

In order to detect such a restriction of its functioning, the following methods may for example be used:
- hardware or software watchdogs
- logical and/or temporal program run monitoring of the software used
- stack monitoring of the software used
- checking of the correct functioning of ROM and RAM memories
- monitoring of the voltage supply
- checking of the integrity of program code and data Since both the structure shown in FIG. 2 and the structure shown in FIG. 9 offer advantages in terms of the implementation of the apparatus according to the invention, it appears to be useful for particularly high security requirements to use a combination of both structures, as shown in FIG. 10. In the configuration shown therein, the control logic 13 can cut the connection of the apparatus 33 according to the invention both to the insecure area 11*b* and to the secure area 11*a* of the communication network 11 by means of the breaker switches 14*a* and 14*b*.

In this case, such a separation by the two breaker switches may take place either in synchronism with one another or independently of one another. As an aid to physical segmentation of the two areas 11*a* and 11*b* of the communication network 11, it may be useful always to allow the switches 14*a* and 14*b* to carry out a closing operation alternately, since in this way the physical segmentation is retained at all times even in the case of a malfunction of the apparatus 33 according to the invention.

In the case of a malfunction of the device 33 being detected by the control logic, it is recommended to open both breaker switches 14a and 14b at the same time and to carry out a reset in order to achieve the defined secure state of the device 33 according to the invention after a restart. The separation from both parts of the communication network 11 should also be the secure state of the medical device 10 and should be assumed by the latter for example in the event of stoppage of the supply voltage of the apparatus 33.

One embodiment of the apparatus according to the invention which is particularly advantageous with regard to security is obtained if the apparatus according to the invention has a redundant structure. A number of possible methods are possible for this.

Figure 11:
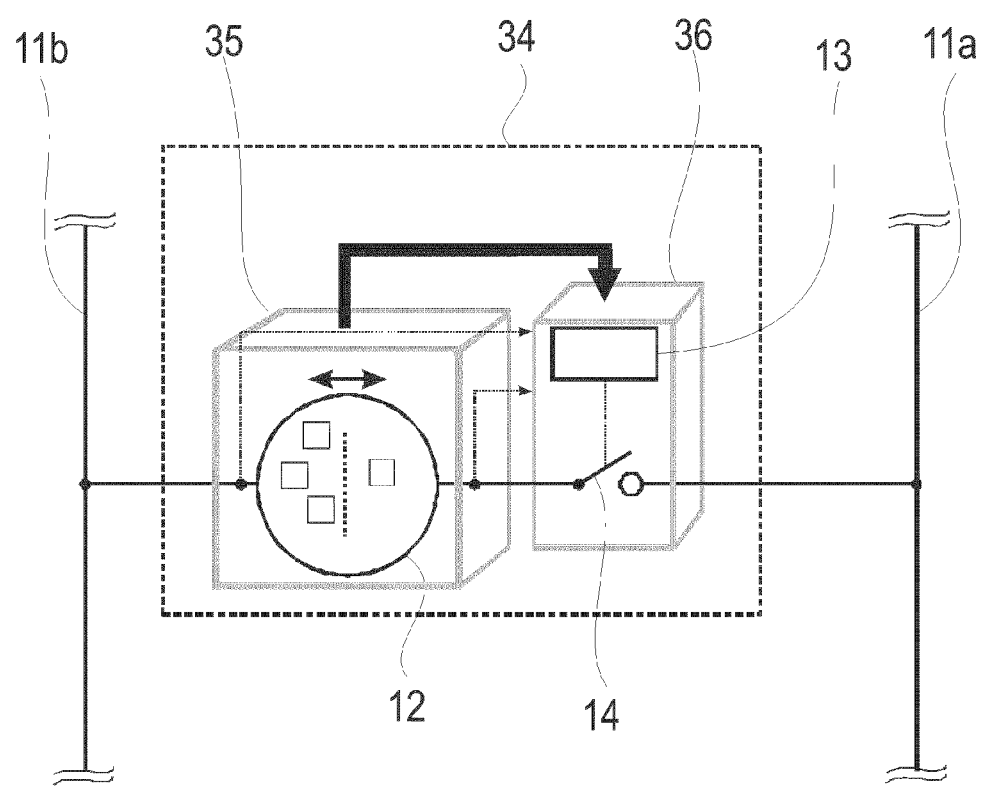
FIG. 11 shows an example of a redundant architecture of an apparatus according to the invention.

FIG. 11 shows one possible redundant implementation of the apparatus according to the invention, which for the sake of simplicity is again shown by way of example with bidirectional packet filtering.

The apparatus 34 according to the invention in this case consists of a working channel 35 and a monitoring channel 36, which are accommodated in separate sub-systems. The working channel 35 performs the functions of the packet filter 12 and all the functions associated therewith, that is to say e.g. also a conversion of the communication protocols used. The monitoring channel 36 does not perform any activity in this respect. Its function is merely to monitor the correct functioning of the working channel 35. This may take place in that a (simplified) model of the task of the working channel exists in the monitoring channel, or the monitoring channel 36 may even check the function of the working channel 35 according to a watchdog principle. If the monitoring channel 36 detects a fault on the working channel 35, it can separate it from the communication network 11 by means of the breaker switch 14 and can optionally trigger a reset in order to bring it back into a defined state in which it thus performs its function.

FIG. 11 shows by way of example a separation on the side of the secure part 17 of the communication network 11; however, variants comprising a separation from the insecure area 11b or from both areas of the communication network 11 are also possible.

One very secure variant consists in completely independent "diversitary" channels, each of which can separate itself and the other channel from the potentially insecure part of the communication network 11 and can monitor the correct functioning of the other channel.

Figure 12:
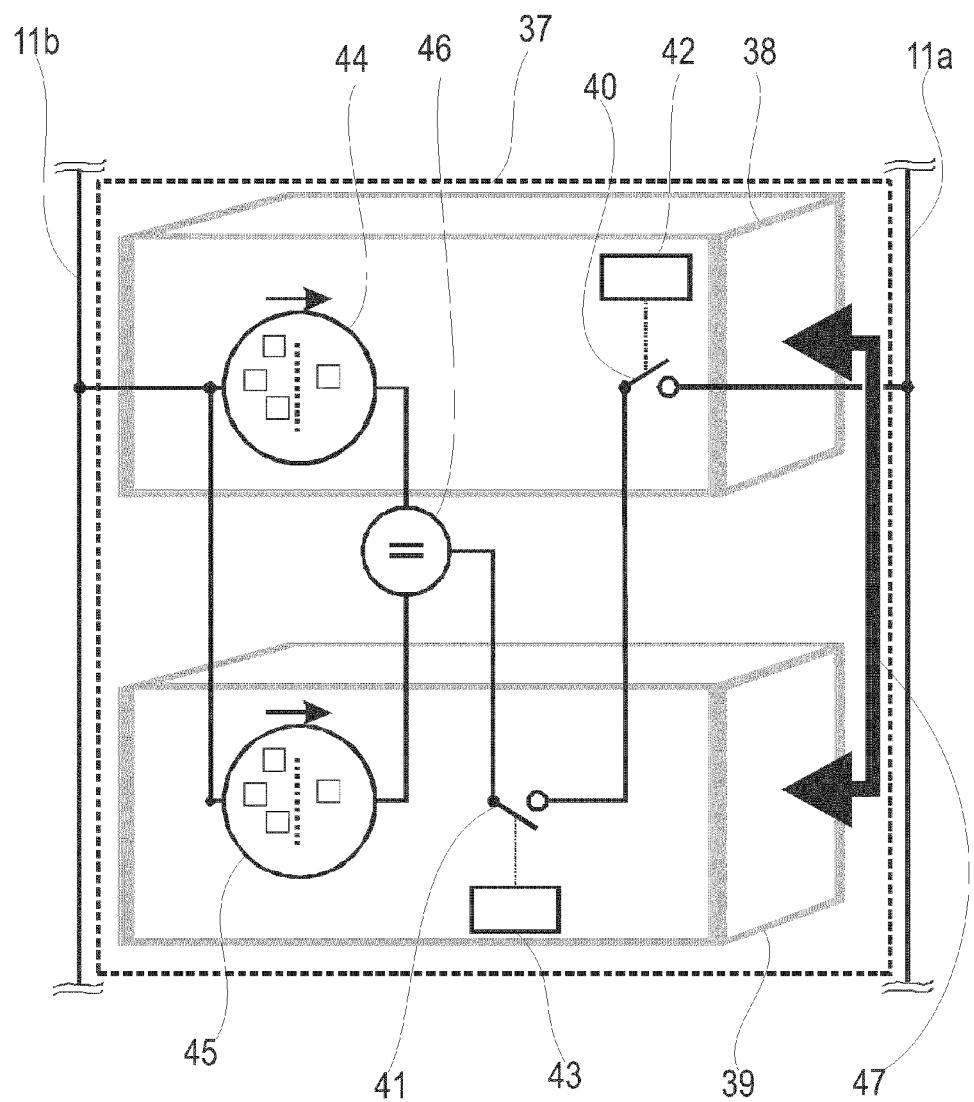
FIG. 12 shows a configuration of an apparatus according to the invention with a diversitary redundant architecture.

Such a variant is shown in simplified form in FIG. 12. The entire part which transports communication packets from the secure area 11a to the insecure area 11b of the communication network 11 is omitted here. In the case of bidirectional packet filtering, it may be formed as a mirror image to the illustrated part, or else by simply forwarding the communication packets. Here, too, a separation takes place by way of example on the side of the secure area 11a of the communication network 11.

The apparatus 37 according to the invention consists of two independent sub-systems 38 and 39 which in each case contain a breaker switch 40 and 41, a control logic 42 and 43 and a packet filter 44 and 45. Once the two packet filters 44 and 45 have reached the result of optionally translating and forwarding a communication packet, the two partial results are checked by a comparator 46 and forwarded if they are identical. The two instances 42 and 43 of the control logic can in each case independently of one another carry out the separation of the two areas 11a and 11b of the communication network 11. For this, they can evaluate information originating from their respective sub-system 38 or 39 regarding any possible attacks that are taking place or regarding a restricted functionality of the respective sub-system. However, it is particularly advantageous if a communication path 47 exists between the two sub-systems 38 and 39, by means of which the two instances 42 and 43 of the control logic receive indications of the correct functioning of the respective other sub-system 39 or 39 so that they can carry out a separation of the parts 11b and 11a of the communication network 11.

In this case, too, it is advantageous if the two instances 42 and 43 of the control logic can trigger a reset of the respective other sub-system or even of the entire apparatus 37.

If, to develop the apparatus 37 according to the invention, use is to be made for example of operating systems in order to minimise the development time and development faults, it is recommended to use independent operating systems and as far as possible also different network hardware in the two channels, since the probability that both channels will be influenced at the same time and in the same way by the potentially insecure communication network 11 is extremely low and thus the security against malfunction is very high. Furthermore, a diversitary design of the described device also has the advantage that errors arising in the design and development of the software and/or hardware thereof or as a result of a random change in data contents of computer memories are usually detected and lead to permanent separation from the potentially insecure communication network 11 until the problem has been corrected.

This therefore minimises the risk that a fault prevents the functioning of the device, but this is not detected before a possible influencing of the medical device by the potentially insecure communication network 11 and the influencing which poses a risk to the patient therefore actually takes place.

Figure 13:
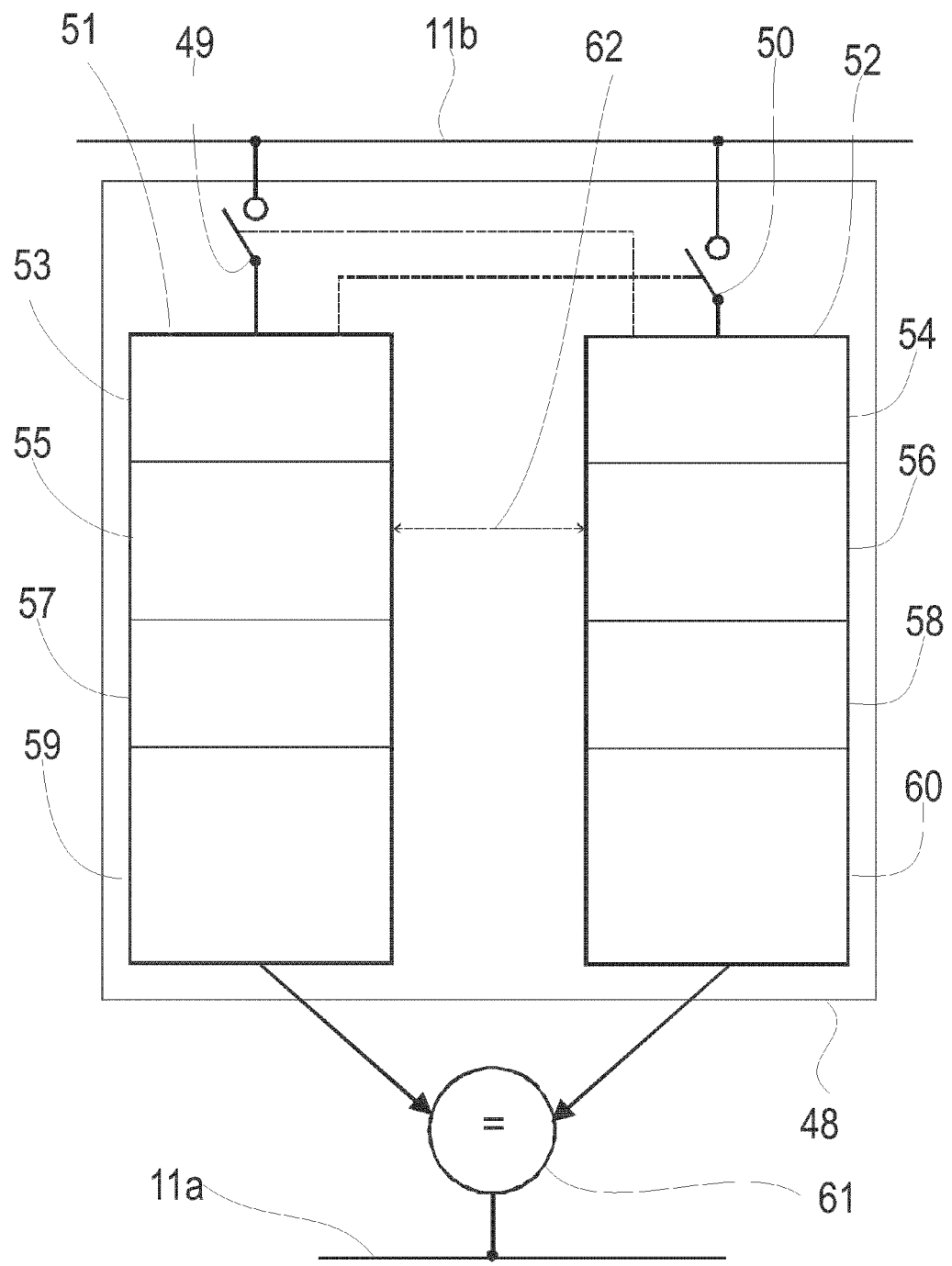
FIG. 13 illustrates a possible diversitary implementation of the apparatus according to the invention.

FIG. 13 shows a possible schematic structure of such a diversitary apparatus 48 according to the invention, again only for one transport direction from the insecure area 11b to the secure area 11a of the communication network 11.

From the insecure area 11b of the communication network 11, the data pass through the operating system 53 in the first channel 51 and from there run through a firewall 55, a virus scanner 57 and the protocol analysis 59. Each of these layers discards the data if they potentially pose a risk. The data then pass into the comparator 61. In parallel with this, the data in the second channel 52 pass through the second operating system 54, the second firewall 56, the second virus scanner 58 and the second protocol analysis 60, likewise into the comparator 61. Only if the two channels have arrived at the result that the data are correct and harmless are said data forwarded to the secure area 11a of the communication network 11. The two channels carry out mutual monitoring 62, optionally with triggering of a reset, and can separate one another from the insecure area 11b of the communication network 11 via the switch-off paths 49 and 50.

Possible embodiments of the described device 9 may be as a stand-alone device or as a device integrated in a medical device. The apparatus 9 according to the invention is usually implemented by a combination of software and dedicated hardware or else as a combination of dedicated firmware and hardware (e.g. by means of an FPGA). An implementation by means of pure software would be conceivable only if the medical device to be monitored already contains the hardware required for implementation.

On many microcontrollers, e.g. a complete separation from the insecure area 11b of the network may take place by switching the I/O pins assigned to communication with the secure area 11*a* of the communication network 11 into a passive mode.

Figure 14:
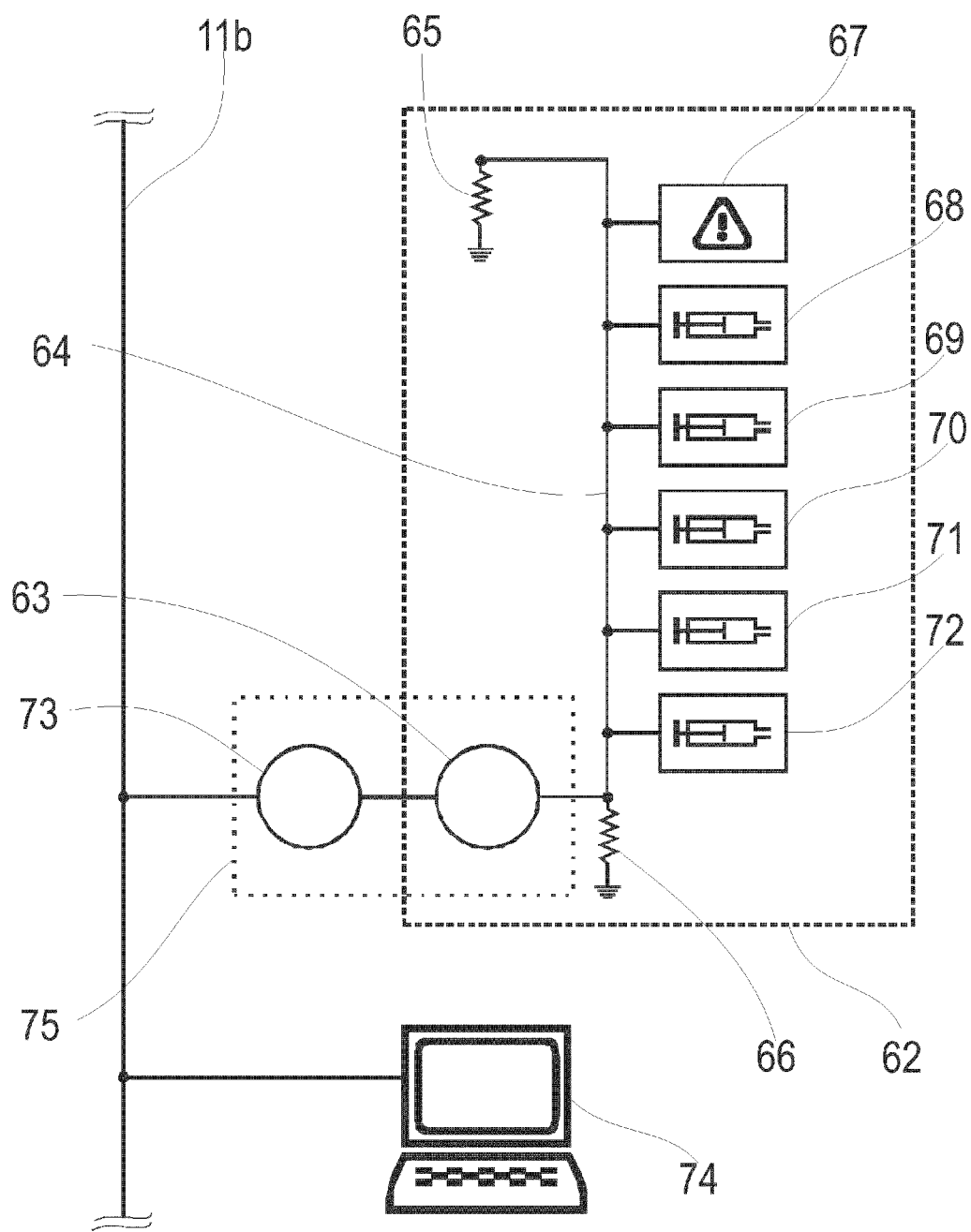
FIG. 14 shows by way of example the protection of a system of infusion pumps against influences from the insecure area of the communication network.

A few possible examples of fields of use of the apparatus according to the invention will be given below:

FIG. 14 shows by way of example and schematically the protection of a system of infusion pumps by the device according to the invention. In the illustrated examples, a system of infusion pumps consists of a communication module 63 which is connected to a central CAN bus 64 with a linear bus topology and terminal resistors 65 and 66, and of a central alarm system 67 and the infusion pumps 68 to 72. The communication module 63 can convert the communication protocol $P_1$ of the infusion pumps 68 to 72 which is used on the CAN bus into another, e.g. Ethernet-based communication protocol $P_2$. Within the context of the above definitions, this system of infusion pumps represents a medical device 62 on account of the additional services (central communication and central alarm) provided by the system. In order to protect it against possible attacks from the insecure area 11*b* of the communication network 11, an apparatus 73 according to the invention is used. Connected to the insecure area 11*b* of the communication network 11 is a PC 74 which can perform activities such as central monitoring of the alarm or central distribution of treatment data.

In this case, it is particularly advantageous to select an apparatus according to the invention with bidirectional packet filtering and an encryption known to the PC 74, in order to avoid possible disclosure of confidential personal data in the insecure part of the network and to be able to prevent unauthorised manipulation of treatment data in the insecure area 11*b* of the communication network 11. In this case, the switches 14*a* and 14 from FIG. 3 can carry out a separation of the Ethernet line if correctly terminated. In this way, the medical device 62 can be physically separated from the insecure area 11*b* of the network 11. In an embodiment according to FIG. 3, the apparatus 73 according to the invention remains connected to the insecure area 11*b* of the communication network 11 and can thus detect (optionally after a dedicated reset) when there is no longer a potential attack on the medical device 62. Only then are the breaker switches closed again and is the medical device 62 reconnected to the insecure area 11*b* of the communication network 11.

It can be seen from this example that security and/or cost advantages may be obtained in an embodiment when the apparatus 73 according to the invention and the communication module 63 are combined to form one unit 75 which combines the functions of the two individual devices. This may be designed in a redundant manner, e.g. with comparable costs, in order to achieve a higher level of security. In contrast to the embodiment comprising two individual devices, it thus possible to avoid even the situation whereby the communication module 63 as a result of a malfunction carries out an attack on the other sub-devices of the medical device 62. Such an apparatus 75 can then be designed as a stand-alone unit or integrated into the medical device 62, e.g. as a plug-in card. In both cases, it is recommended to allow the switches 14*a* and 14*b* to carry out a separation from the (already correctly terminated) CAN bus 64.

A further example that may be mentioned is the connection of a group of patient monitors to a central monitor.

Particular advantages can be obtained by using the apparatus according to the invention when an existing older medical device is to be networked again—e.g. after moving to a different building. The older devices often still have serial interfaces (e.g. RS-485) which require a direct connection between all the participating communication partners. Such a networking of a plurality of patient monitors, which are connected to a central monitor 76, is shown by way of example in FIG. 15.

The central monitor 76 is linked to the connected patient monitors 82 to 86 via a number of serial RS-485 interfaces 77 to 81. For each individual connection, a dedicated cable must be installed between the central monitor 76 and the respective patient monitor.

Figure 16:
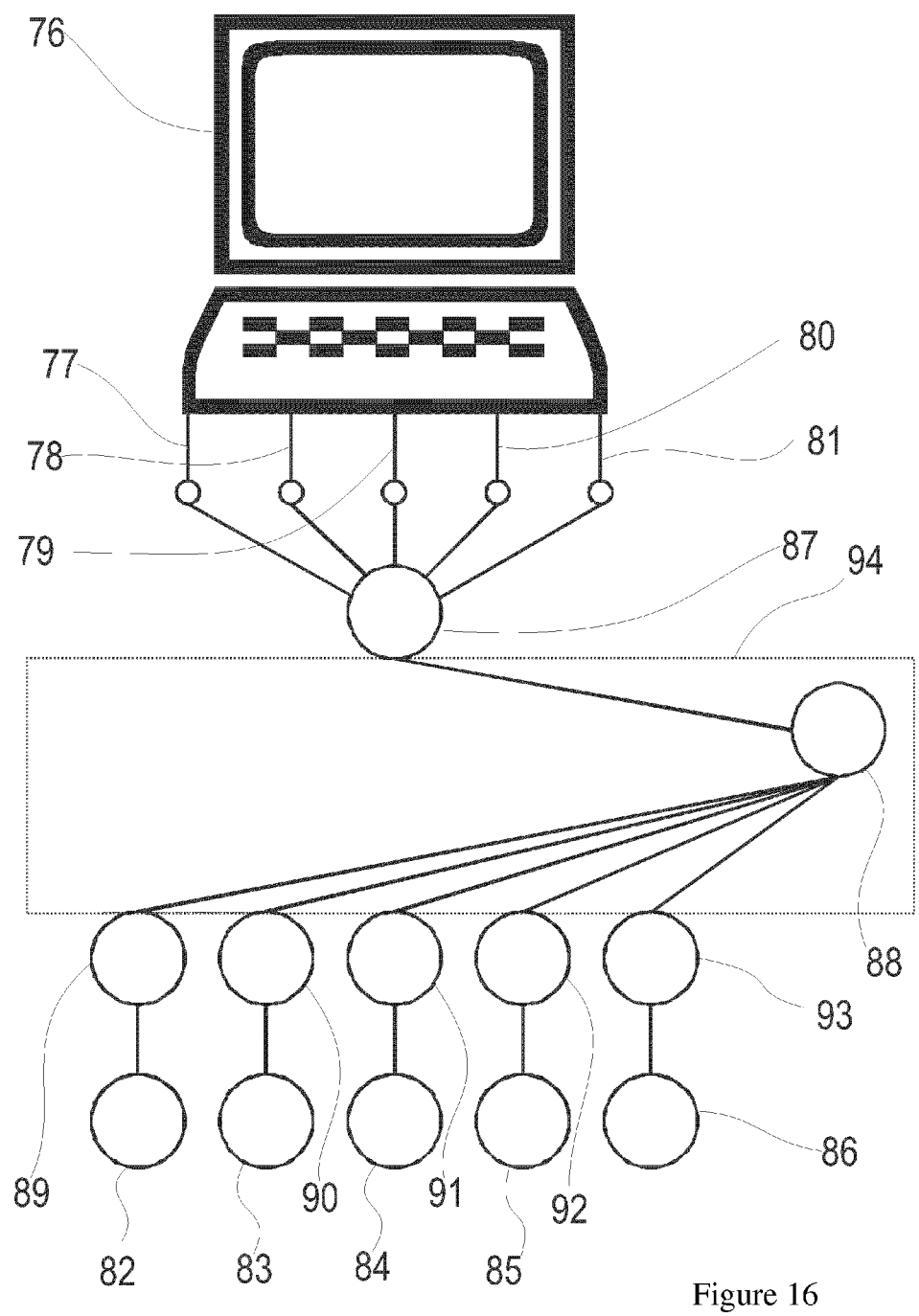
FIG. 16 illustrates the connection of patient monitors to a central monitor via apparatuses according to the invention.

If it can be imagined that many other groups of medical devices in addition to the patient monitoring also have to be networked within a medical establishment, the high costs of such a procedure are obvious. Accordingly, FIG. 16 shows the resulting structure using the apparatus according to the invention and an existing Ethernet infrastructure.

The central monitor 76 is now connected to an apparatus 87 according to the invention, which has a plurality of RS-485 interfaces. The apparatus 87 according to the invention is connected to an Ethernet switch 88, to which the apparatuses 89 to 93 according to the invention are connected. The patient monitors 82 to 86 are in turn connected to the RS-485 interfaces thereof.

Figure 15:
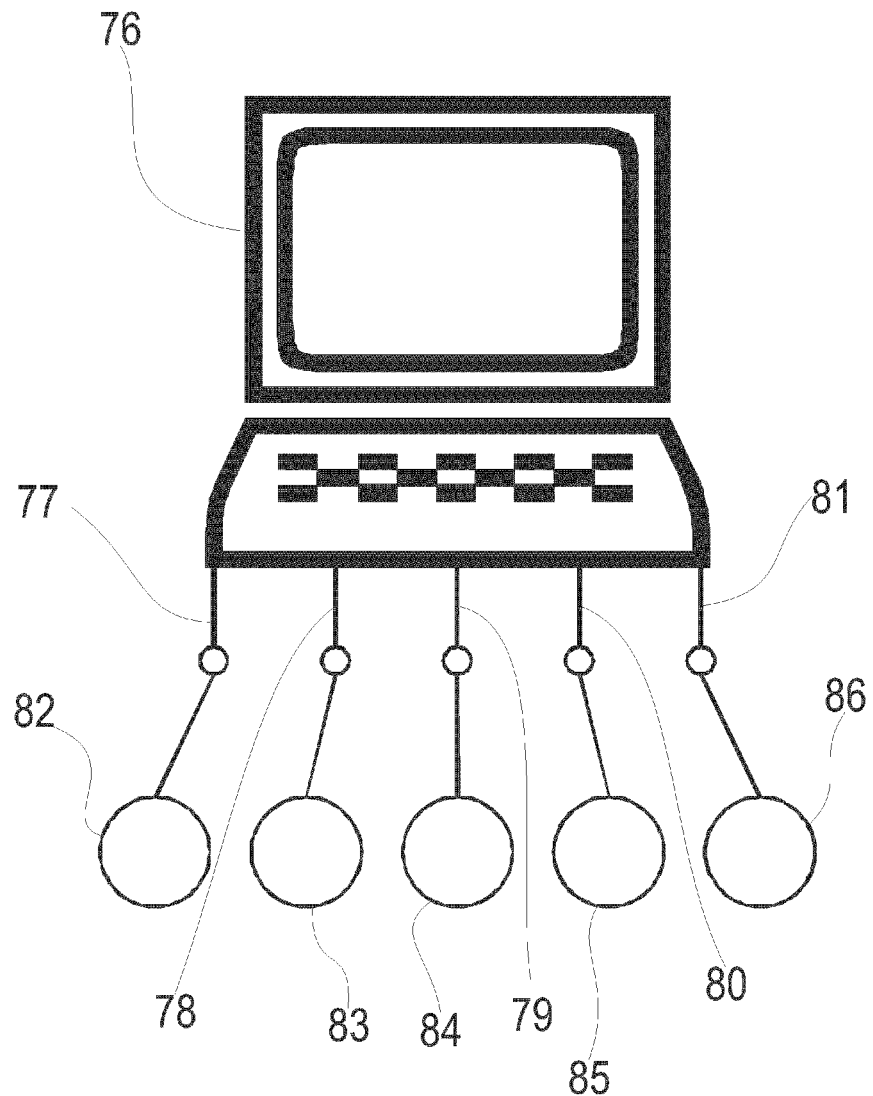
FIG. 15 shows the conventional way of connecting patient monitors to a central monitor.

At first, this type of connection or cabling appears to be much more complicated than the star-shaped cabling from FIG. 15. However, it is important to realise that the components and connections of the communication network 11 which are located in the box 94 shown in dotted line form part of the IT infrastructure of any modern medical establishment and thus can be used without any significant additional costs. Furthermore, such a networking structure makes it possible very easily to move patients and/or central monitors, since these can simply be plugged together with their apparatuses according to the invention into other Ethernet sockets of the medical establishment. The use of the apparatuses 87 and 89 to 93 according to the invention may in this case ensure the following for example:

The original RS-485 communication data are transported in enveloping TCP/IP packets via the Ethernet.

The data are protected against unauthorised visibility in the Ethernet by means of encryption.

The data are protected against unauthorised falsification in the Ethernet.

Due to changing data within the enveloping TCP/IP packets, packets stored by other network participants cannot be used at a later point in time.

A temporal response which the systems 76 and 82 to 86 can achieve in the case of serial communication (e.g. response times to signs of life, which due to technical conditions are often responded to and thus also expected much more quickly than would be necessary for risk reasons), but which in principle cannot be guaranteed in the case of transport via the Ethernet, is guaranteed by the apparatuses according to the invention by means of caching and proxying. Only when an actual communication disruption is detected (due to the stoppage of the signs of life from the other medical device) are the responses to the signs of life no longer transmitted by the apparatuses according to the invention.

Different groups of patient monitors and central monitors, as originate e.g. from different stations, cannot influence one another within the communication network 11 of the medical establishment.

In the case of potentially harmful data traffic in the Ethernet, the patient monitors and the central monitor are separated from the Ethernet. This makes the central monitor inoperable, but the local functionality of the patient monitors is retained.

With reference to FIG. 16, it can be seen that the apparatus according to the invention should advantageously be made available in a large number of different configurations. Such configurations may differ for example in:

- the type of physical transmission principles used on the input or output side,
- the type of communication protocol used,
- the type of application protocol used,
- the number of different inputs and outputs of the apparatus according to the invention,
- the additional temporal and/or logical conditions for opening the breaker switches,
- the additional temporal and/or logical conditions for closing the breaker switches, and
- the additional temporal and/or logical conditions for carrying out a reset of the device according to the invention.

Such a large number of possible configurations can advantageously be produced by using modular concepts for the apparatus according to the invention. One example of such a modular apparatus according to the invention is shown in FIG. 17.

The modular apparatus 103 according to the invention consists of the packet filter module 94, which contains the bidirectional packet filter 12, and two driver modules 95 and 96 which are in each case connected independently to one side of the packet filter module via a communication interface. The driver modules 95 and 96 each contain a driver 97 and 98 which carries out a conversion into the required physical media and optionally an implementation of the lower levels of the communication protocol. The driver modules 95 and 96 also contain in each case a control logic 99 and 100 which actuate the breaker switches 101 and 102 and can optionally trigger a reset of the apparatus 103 according to the invention.

Such a modular structure of the apparatus according to the invention considerably simplifies adaptation to various applications. In this case, it is particularly useful also to design the software of the apparatus according to the invention in a modular manner, e.g. by implementing a driver architecture for actuating the various driver modules. It is also highly advantageous to develop a code generator or an API/a framework by means of which the various tasks of the packet filter can be easily implemented at different levels of the ISO/OSI model or an application protocol level, regardless of the precise structure of the apparatus according to the invention.

Figure 17:
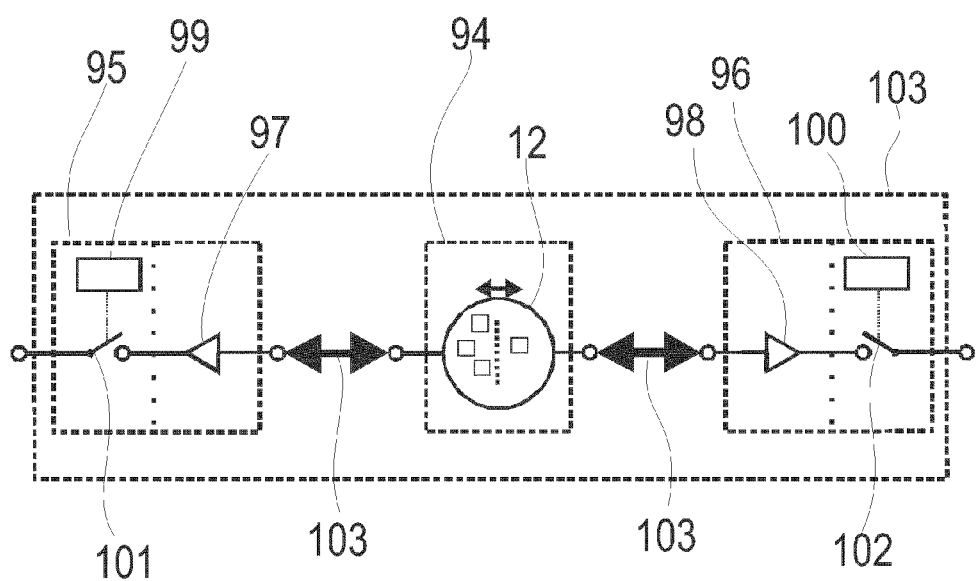
FIG. 17 illustrates schematically and by way of example an apparatus according to the invention of modular design.

As modifications to the modular apparatus according to the invention shown in FIG. 17, it may be advantageous—particularly with a redundant implementation—if the security logics 99 and 100 are partially contained in the packet filter module 94 and the simplified parts of the control logic contained in the driver modules can cause the respective breaker switch to open or close via the respective communication interface.

Figure 18:
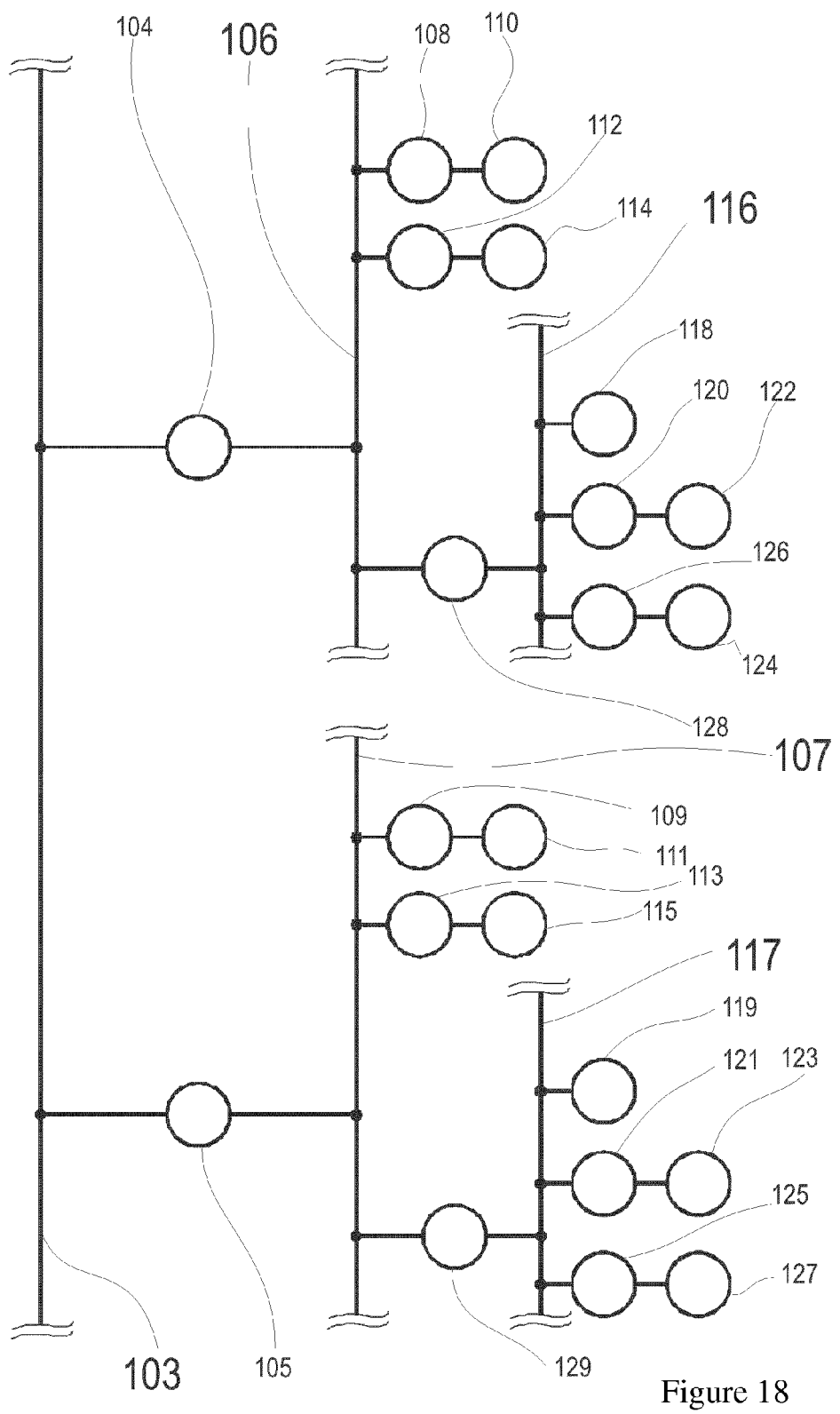
FIG. 18 illustrates by way of example the hierarchical protection of a medical establishment by means of the present invention.

A use of the apparatus according to the invention within a medical establishment may be used for medical devices/systems consisting of a plurality of networked sub-networks, together with known network technologies, to obtain hierarchical protection of sub-areas of the communication network 11 by dividing it into various security areas. Such a hierarchical protection by an apparatus according to the invention is shown by way of example in FIG. 18.

The communication networks 106 and 107 of two locations within a medical establishment are connected to one another via two devices 104 and 105 with firewall and VPN functionality via the Internet. A central monitor 110 is connected to the communication network 106 via an apparatus 108 according to the invention, and an accounting PC 114 is connected to said network via a device 112 with firewall and VPN functionality. By way of example, the intensive care room A, which is to be considered here as a medical device, is connected to its communication network 116 via the apparatus 128 according to the invention. A prescription PC 118 and, via the apparatuses 120 and 124, an infusion pump system 122 and a patient monitor 126 are connected thereto. The patient monitor 126 supplies the patient data to the central monitor 110 so that said data can be observed together with the patient data from other patient monitors on the central monitor. The prescription PC 118 serves to transmit entire lists of infusion data to the infusion pump system 122 for distribution to the individual pumps. This makes it possible to conveniently configure all the pumps of the infusion pump system 122 for starting or adapting the infusion treatment. The prescription PC 118 may also optionally serve to transmit data to other infusion pump systems located in the same intensive care room. The same structure of communication network 11 exists on the communication network 107 of the second location. A central monitor 111 is connected to said network via an apparatus according to the invention and an accounting PC 115 is connected via a device 113 with firewall and VPN functionality. Via the apparatus 129 according to the invention, the intensive care room B is connected to its communication network 117. Within the latter, a prescription PC and, via the apparatuses 121 and 125 according to the invention, an infusion pump system 123 and a patient monitor 127 are connected.

This network architecture can be used for example for the following communication paths:

- Location A and location B share a common communication network 11 which consists of two parts 106 and 107. A VPN is used so that no data can be seen or manipulated in an unauthorised manner in the Internet. The firewalls in 104 and 105 protect the two communication networks 11 against attacks from the Internet.
- The accounting PCs 114 and 115 are connected to one another via a VPN. This prevents the confidential data from being able to be seen or manipulated by unauthorised persons within the parts 106 and 107 of the communication network 11. Since a not inconsiderable amount of malware and associated attacks reach a network via data carriers behind the firewalls of companies, protection of the area of the communication network 11 which is critical to the success of the medical establishment by the firewalls in the devices 112 and 113 is useful here.
- Within the intensive care room A, the infusion pump system 122 communicates with the prescription PC 118 via the communication network 116. Since other devices which pose a potential risk to the infusion pump system 122 may also be connected to this part of the communication network 11—even the prescription PC might be infested with malware via data carriers—said infusion pump system is protected by an apparatus 120 according to the invention.
- A patient monitor which is protected by the apparatus 124 according to the invention can carry out communication with the central monitor which is protected by the apparatus 108 according to the invention.
- In order to minimise the influence of other communication participants in the communication network 106, the apparatus 128 according to the invention allows into the intensive care room A only those communication packets which are actually relevant for the medical devices located therein.

A few reactions to possible attacks will now be described. Here, it is assumed that the attacks address all the devices connected to the system and are detected by the control logic of the respective apparatuses as being so serious that merely suppressing communication packets through the respective packet filter does not appear to be sufficient, but rather the respective breaker switch is opened.

In the event of an attack within the communication network 116, the apparatus 120 according to the invention actuates the breaker switch so that the infusion pump system 122 can continue its infusions undisturbed, but communication with the prescription PC 118 is no longer possible. In this situation, the apparatus 124 according to the invention likewise actuates the breaker switch so that the patient monitor 126 likewise continues the monitoring functionality undisturbed, but communication with the central monitor 110 is no longer possible. Furthermore, the apparatus 128 according to the invention likewise actuates the breaker switch and thus does not allow the attack to influence the rest of the communication network 106. The functionality of other intensive care rooms, in which the attack does not occur within their own network, is thus ensured in an undisrupted manner, and also the central monitor 110 can communicate undisturbed with the patient monitors in the other intensive care rooms.

In the event of an attack coming from the communication network 106, the breaker switches of the apparatuses 112 and 128 according to the invention are actuated. The central monitor thus has no connection to the patient monitor 126 and also not to patient monitors in other intensive care rooms. However, the communication within the communication network 116 remains undisturbed, so that use of the prescription PC 118 together with the infusion pump system 122 continues to be fully retained.

Such a hierarchical use of the apparatuses according to the invention makes it possible, in the event of attacks, only to provide the functionality that is absolutely necessary and at the same time to minimise the effects on other participants in the communication network, and thus to increase the availability thereof.

All the features disclosed in the application documents are claimed as essential to the invention in so far as they are novel individually or in combination with respect to the prior art.

LIST OF REFERENCES 1 patient's home
2 medical establishment
3 WAN network
4 data-acquiring medical device
5 LAN network
6 LAN network of the medical establishment
7 evaluating medical device
8 insecure area of the communication network from the point of view of the medical establishment
9 apparatus according to the invention
10 medical device
11 communication network
11a secure area
11b insecure area
12 packet filter
13 control logic
14 breaker switch
15, 16 medical sub-devices
18 bidirectional packet filter
19 patient monitor central system
20, 21, 22 patient monitors
26 transmitted communication packet
27 modified communication packet
28 additional data
29 communication packet that can be used by the medical device
30 encrypted data region
31 encrypted modified communication packet
32 apparatus according to the invention with breaker switch for the insecure area of the communication network
33 apparatus according to the invention with breaker switches on both sides
35 working channel
36 monitoring channel
37 apparatus according to the invention with two independent sub-systems
38, 39 independent sub-systems
40, 41 breaker switches
42, 43 control logic
44, 45 packet filters
46 comparator
47 communication path between the sub-systems
48 diversitary device according to the invention
49, 50 breaker switches
51, 52 first and second channel
53, 54 first and second operating system
55, 56 first and second firewall
57, 58 first and second virus scanner
59, 60 first and second protocol analysis
61 comparator
62 medical devices
63 communication module
64 CAN bus
65, 66 terminal resistors
67 alarm system
68-72 infusion pumps
73 apparatus according to the invention
74 PC
75 unit consisting of apparatus 75 according to the invention and communication module 63
76 central monitor
77-81 RS-485 interfaces
82-86 patient monitors
87 apparatus according to the invention
88 Internet switch
89-93 apparatuses according to the invention
94 unit consisting of components and connections of the communication network
95, 96 driver modules
97, 98 drivers
99, 100 security logic
101, 102 breaker switches
103 device according to the invention
104, 105 devices with firewall and VPN functionality
106, 107 communication networks of two locations in a medical establishment
108, 109 apparatus according to the invention
110, 111 central monitor
112, 113 device with firewall and VPN functionality
114, 115 accounting PCs
116, 117 communication networks
118, 119 prescription PCs
120, 121 apparatuses according to the invention
122, 123 infusion pump systems
124, 125 apparatuses according to the invention
126, 127 patient monitors
128, 129 devices according to the invention

The invention claimed is:

1. An apparatus comprising:
a transmission means for transmitting communication packets to and from an external device via a communication network, the communication network comprises at least one insecure sub-network and a secure sub-network on the device side;
a monitoring means for monitoring the state of the connection of the device to the network; and
a breaker means for breaking an existing connection between the secure sub-network and the insecure sub-network,
wherein the external device is a medical device comprising a means for connecting to the communication network,
wherein the apparatus is suitable for breaking the network connection to the medical device if, during monitoring, a state of the network connection is detected which poses a risk to a patient treated with the device or to the correct functioning of the device
wherein the apparatus carries out at least one of a translation or encryption of communication protocols used in the insecure sub-network or in the secure sub-network in such a way that communication packets that have been modified with respect to the communication packets originating from the original protocol are used in the respective other sub-network.

2. The Apparatus according to claim 1, wherein the transmission means comprises a packet filter which carries out packet filtering on the communication packets transmitted between the insecure sub-network and the secure sub-network of the communication network 11, wherein the packet filter is suitable for blocking communication packets which pose a potential risk to the medical device, the breaker means comprises at least one breaker switch, and the monitoring means comprises at least one control logic which, when a state of the network connection which poses a risk to a patient or to the correct functioning of the device is detected, triggers opening of one of the breaker switches so as to separate the insecure sub-network from the secure sub-network of the communication network which is connected directly to the medical device.

3. The Apparatus according to claim 2, wherein the packet filter performs bidirectional packet filtering on the communication packets transmitted between the insecure sub-network and the secure sub-network of the communication network.

4. The Apparatus according to claim 2, wherein the packet filter partially or completely replaces at least one of the monitoring means or the breaker means by blocking harmful communication packets or all communication packets when a state of the network connection which poses a risk to the patient or to the correct functioning of the device is detected.

5. The Apparatus according to claim 1, wherein the separation between the secure sub-network and the insecure sub-network of the communication network is implemented as logical segmentation.

6. The Apparatus according to claim 1, wherein the separation between the secure sub-network and the insecure sub-network of the communication network is implemented as physical segmentation.

7. The Apparatus according to claim 6, wherein physical segmentation is achieved by different physical transmission paths in the secure sub-network and in the insecure sub-network of the communication network or by different instances of the same transmission path.

8. The Apparatus according to claim 6, wherein the communication network comprises at least one of cable-based or radio-based transmission paths.

9. The Apparatus according to claim 1, wherein the transmission path in the secure sub-network of the communication network comprises optical fibers.

10. The Apparatus according to claim 2, wherein the control logic includes means for carrying out a static and/or dynamic check of the data to be transmitted in the communication network, the result of which check leads to an existing connection between the secure sub-network and the insecure sub-network of the network being maintained or cut by triggering the breaker switch(es).

11. The Apparatus according to claim 2, wherein one of the breaker switches is located on one of the sides connected to the secure sub-network of the communication network or on the side of the apparatus connected to the insecure area of the communication network, so as to be able to separate only the medical device or both the medical device and the apparatus itself from the insecure sub-network.

12. The Apparatus according to claim 1, further comprising a redundant architecture by integrating in the monitoring means a model of the function of the transmission means which makes it possible to check the correct functioning thereof.

13. The Apparatus according to claim 1, further comprising at least two diverse channels, each with their own monitoring means and breaker means, wherein each channel can monitor both itself and also the other channel independently and can separate from the insecure sub-network of the communication network when a state of the network connection which poses a risk to the patient or to the correct functioning of the device is detected.

14. The Apparatus according to claim 2, further comprising a comparator for comparing the results of the packet filtering in each channel with one another and forwarding the communication packets to be transmitted only if they are the same in each channel.

15. The Apparatus according to claim 13, further comprising in each channel a security logic which is suitable for separating the insecure area of the communication network from the secure area thereof, independently of the security logic of any other channel, when a state of the network connection which poses a risk to the patient or to the correct functioning of the device is detected.

16. A method for controlling an apparatus for interacting with a medical device which is suitable for connection into a communication network which comprises at least one insecure sub-network and a secure sub-network on the device side, the secure area being protected by a firewall device, the method comprising:
ensuring the transmission of communication packets to and from the medical device via the communication network's;
monitoring the state of the connection of the device to the network; and
breaking an existing connection between the secure sub-network and the insecure sub-network of the network if during the monitoring process, a state of the network connection is detected which poses a risk to the patient or to the correct functioning of the device.

17. The method according to claim 16, further comprising packet filtering during the transmission of the communication packets transmitted between the insecure sub-network and the secure sub-network of the communication network, wherein filtering is suitable for blocking communication packets which pose a potential risk to the medical device.

18. The method according to claim 16, further comprising bidirectional packet filtering on the communication packets transmitted between the insecure sub-network and the secure sub-network of the communication network.

19. The method according to claim 16, further comprising allowing logical segmentation between the secure area and the insecure area of the communication network.

20. The method according to claim 16, further comprising allowing said monitoring and/or breaking steps to be partially or completely replaced by the packet filtering during the transmission by blocking, during the packet filtering, harmful communication packets or all communication packets when a state of the network connection which poses a risk to the patient or to the correct functioning of the device is detected.

21. The method according to claim 16, wherein packet filtering is suitable for carrying out one of a translation or encryption of the communication protocols used in the insecure sub-network or in the secure sub-network of the communication network in such a way that communication packets that have been modified with respect to the communication packets originating from the original protocol are used in the respective other sub-network of the communication network.

22. The method according to claim 16, wherein monitoring includes performing one of a static or dynamic check of the data to be transmitted in the communication network is carried out, the result of which check leads to an existing connection between the secure sub-network and the insecure sub-network of the network being maintained or cut.

23. The method according to claim 16, further comprising operating redundantly by integrating in the monitoring step an at least partial model of the function of the transmission step which makes it possible to check the correct functioning thereof.

24. The method according to claim 16, further comprising operating in at least two diverse channels, each with their own transmission, monitoring and breaking, wherein each channel can monitor both itself and also the other channel independently and can separate from the insecure sub-network of the communication network when a state of the network connection which poses a risk to the patient or to the correct functioning of the device is detected.

* * * * *